US008524762B2

(12) United States Patent
Nawrocki et al.

(10) Patent No.: US 8,524,762 B2
(45) Date of Patent: Sep. 3, 2013

(54) THIOXANTHONE-BASED AUTOPHAGY INHIBITOR THERAPIES TO TREAT CANCER

(75) Inventors: Steffan Nawrocki, San Antonio, TX (US); Jennifer Carew, San Antonio, TX (US); Guru Reddy, Irvine, TX (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 95 days.

(21) Appl. No.: 13/043,333

(22) Filed: Mar. 8, 2011

(65) Prior Publication Data

US 2011/0275696 A1 Nov. 10, 2011

Related U.S. Application Data

(60) Provisional application No. 61/311,736, filed on Mar. 8, 2010.

(51) Int. Cl.
*A61K 31/38* (2006.01)

(52) U.S. Cl.
USPC ......................................................... 514/437

(58) Field of Classification Search
USPC ......................................................... 514/437
See application file for complete search history.

(56) References Cited

U.S. PATENT DOCUMENTS

| | | | |
|---|---|---|---|
| 6,391,911 B1 | 5/2002 | Bases | |
| 6,767,919 B2 * | 7/2004 | Walker et al. | 514/437 |
| 7,799,782 B2 * | 9/2010 | Munson et al. | 514/234.5 |
| 2004/0018968 A1 | 1/2004 | Sgouros | |
| 2008/0269261 A1 | 10/2008 | Ryan et al. | |
| 2009/0221615 A1 | 9/2009 | Reddy | |

FOREIGN PATENT DOCUMENTS

| | | |
|---|---|---|
| WO | WO0050031 | 8/2000 |
| WO | 2007/071970 | 6/2007 |

OTHER PUBLICATIONS

Brech et al. "Autophagy in tumour suppression and promotion" Molecular Oncology 3 (2009) 366-375.
Lee et al. "Histone deacetylase inhibitors in cancer therapy" Current Opinion in Oncology 2006, 20:639-649.
Leyton et al. "In vivo Biological Activity of the Histone Deacetylase Inhibitor LAQ824 Is Detectable with 3'-[18F] Fluorothymidine Positron Emission Tomography." Cancer Res 2006; 66:(15). Aug. 1, 2006.
Luo et al. "Inhibition of the Human Apurinic/Apyrimidinic Endonuclease (Ape1) Repair Activity and Sensitization of Breast Cancer Cells to DNA Alkylating Agents with Lucanthone." Anticancer Research 24: 2127-2134 (2004).
Mendez et al. "Abasic Sites in DNA of HeLa Cells Induced by Lucanthone." Cancer Investigation vol. 20, Nos. 7 & 8, pp. 983-991, 2002.
White et al. "The Double-Edged Sword of Autophagy Modulation in Cancer." Clin Cancer Res 2009;15(17) Sep. 1, 2009.

Anonymous, Spectrum Pharmaceuticals Presents Data on Lucanthone, A Novel Anticancer Drug, at the Meeting of the American Association of Cancer Research [on-line] Apr. 17, 2008, retrieved from the internet on Apr. 28, 2009: URL: http://www.istockanalyst.com/article/viewiStockNews/articlesid/2232530, entire document.
Fossella, F.V., Premetrexed for Treatment of Advanced Non-Small Cell Lung Cancer, Seminars Oncol. 31(1): 100-105 (2004).
Hanauske A.R., et al., Premetrexed Disodium : A Novel Antifolate Clinically Active Against Multiple Solid Tumors, Oncol. 6(4): 363-373 (2001).
Reddy, G., et al., Lucanthone Potentiates the Anti-Tumor Activity of Premetrexed in Lung Cancer Model, Pro. Amer. Assoc. Cancer Res. 49: 1349 (2008).
Rochetti, et al., Testing Additivity of Anticancer Agents in Pre-Clinical Studies: A PK/PD Modeling Approach, Eur. J. Cancer 45(18): 3336-3346 (2009).
Carew, J., et al., Lucanthone is a Novel Inhibitor of Autophagy that Induces Cathespin D-mediated Apoptosis, J. Biol. Chem. 286(8): 6602-6613 (2011).
Faivre, S., et al., Molecular Basis for Sunitinib Efficacy and Future Clinical Development, Nature Rev. 6(9): 734-745 (2007).
Luo, M., et al., Inhibition of the Human Apuric/Apyrimidinic Endonuclease (APEI) Repair Activity and Sensitization . . . , Anticancer Res. 24(4): 2127-2134 (2004).
Ma, X., et al., Histone Deacetylase Inhibitors: Current Status and Overview of Recent Clinical Trials, Drugs 69(14): 1911-1934 (2009).
Miller, W., Molecular Targets of Arsenic Trioxide in Malignant Cells, Oncologist 7(1): 14-19 (2002).
Murgo, A., et al., Clinical Trials of Arsenic Trioxide in Hematologic and Solid Tumors: Overview of the NICRD, Oncologist 6(2): 22-28 (2001).
Remiszewski, S., et al., Inhibitors of human Histone Deacetylase: Synthesis and Enzyme and Cellular Activity of Straight Chain Hydroxamates, J. Med. Chem. 45(4) 753-757 (2002).
Savickiene, J., et al., The Novel Histone Deacetylase Inhibitor BML-210 Exerts Growth Inhibitory, Proapoptotic and Growth . . . , Eur. J. Pharmacol. 549(1-3): 9-18 (2006).
Amaravadi, et al., "Principles and Current Strategies for Targeting Autophagy for Cancer Treatment." Clin Cancer Res 2011; 17:654-666.
Emert-Sedlak, et al., "Involvement of cathepsin D in Chemotherapy-induced cytochrome c release, caspase activation, and cell death." Mol Cancer Ther 2005;4:733-742.
Kirkegaard, et al., "Lysosomal involvement in cell death and cancer." Biochimica et Biophysica Acta 1793 (2009) 746-754.
Yang, et al., "The Role of Autophagy in Cancer: Therapeutic Implications." Mol Cancer Ther 2011;10:1533-1541.

* cited by examiner

*Primary Examiner* — Rei-tsang Shiao
(74) *Attorney, Agent, or Firm* — K&L Gates LLP; Louis C. Cullman; Hal Gibson

(57) ABSTRACT

The present specification provides compositions comprising a thioxanthone-based autophagy inhibitor and/or a cancer therapeutic autophagy inducing compound, pharmaceutical kits comprising these compositions, and methods of treating cancer using such compounds, compositions and kits. Additionally, the present specification provides methods of treating cancer using a thioxanthone-based autophagy inhibitor and a radiotherapy.

21 Claims, 15 Drawing Sheets

US 8,524,762 B2

THIOXANTHONE-BASED AUTOPHAGY INHIBITOR THERAPIES TO TREAT CANCER

PRIORITY CLAIM

This patent application claims priority pursuant to 35 U.S.C. §119(e) to U. S. Provisional Patent Application Ser. No. 61/311,736 filed Mar. 8, 2010, which is hereby incorporated by reference in its entirety.

INTRODUCTION

Cancer is the second leading cause of death in the U.S., with 1,228,600 new cases and 564,800 deaths estimated for 1998. Over the past 50 years, the death rate from cancer has increased steadily, due mainly to a large rise in lung cancer death rates resulting from smoking. Cancer occurs in people of all ages, but its occurrence increases greatly in people over 45 years of age. However, cancer is the leading cause of death in the United States for people between the ages of 35 and 65 and it is also the leading cause of non-accidental death among U.S. children under age 15. Men have a higher mortality rate due to cancer than women, and blacks have the highest cancer mortality rate of any major racial group. In the U.S., men have about a 1 in 2 lifetime risk of developing cancer and women have about a 1 in 3 lifetime risk. With the anticipated continued decrease in deaths from heart disease and strokes, cancer will become the overall leading cause of death for the entire American population by the year 2010.

Diagnosis of cancer usually requires a histological examination of a tissue biopsy specimen by a pathologist, although the initial indication of malignancy can be symptoms or radiographic imaging abnormalities. Once diagnosed, cancer is commonly treated by surgery, chemotherapy, radiotherapy, or targeted therapies like immunotherapy, hormonal therapy, or angiogenesis inhibitor therapy. The choice of therapy depends upon the location and grade of the tumor and the stage of the disease, as well as the general state of the patient (performance status). Furthermore, depending on the type and stage of the cancer, two or more of these types of cancer treatments may be combined at the same time or used after one another. Although complete removal of the cancer without damage to the rest of the body is the goal of treatment, current approaches to treating cancer have met with limited success. With respect to surgery, this is due, in part, to the propensity of individual or small numbers of cancer cells to invade adjacent tissue or metastasis to distant sites, thereby limiting the effectiveness of local surgical treatments. The effectiveness of chemotherapy and radiotherapy is often limited by toxicity to or damage of normal tissues in the body. Therefore, compounds, compositions, and methods that can provide a more effective treatment of cancer would be highly desirable. In addition, compounds, compositions, and methods that can treat a particular type of cancer for which no current therapy exists would also be highly desirable.

Autophagy (macroautophagy or autophagocytosis), is a catabolic process by which cells degrade damaged, redundant, or otherwise unnecessary cytoplasmic components including proteins and organelles through the lysosomal machinery. A tightly-regulated process, this degradation pathway is induced under nutrient deprivation, metabolic stress or microenvironmental conditions to ensure energy balance, clearance of damaged proteins and adaptation to stress. Autophagy plays a part in normal cell growth and development, helping to maintain a balance between the synthesis and degradation of cellular components. Additionally, this process provides breakdown products that can serve as an alternative energy source during periods of metabolic stress to maintain homeostasis and viability. As such, autophagy plays a cytoprotective role in situations of nutrient starvation.

The self-cannibalization process involves encapsulation of a portion of the cell's cytoplasm in a double-membrane bound vesicle called an autophagosome or autophagic vacuole, sequestering components including proteins and organelles from the rest of the cytoplasm. Autophagosomes form from the elongation of small membrane structures known as autophagosome precursors. This formation is initiated by class III phosphoinositide 3-kinase and autophagy-related gene (Atg) 6 (also known as Beclin-1). Enlargement of these autophagosome precursors requires the participation of 2 ubiquitin-like conjugation systems that produce modified complexes of autophagy regulators. One involves the conjugation of ATG12-ATG5-ATG16 complex and the other of phosphatidylethanolamine (PE) to LC3/ATG8 and the ATG4 protease complex. Nucleation, expansion, uncoating then occur to complete the formation of the autophagosome. The outer membrane of the autophagosome then fuses in the cytoplasm with a lysosome to form an autolysosome or autophagolysosome where their contents are degraded via acidic lysosomal hydrolases. The final outcome of autophagy activation is highly dependent on the cellular context and the strength and duration of the stress-inducing signal.

The breakdown products of cytoplasm and organelles including amino acids, lipids nucleic acids, and sugars, are exported from lysosomes by permeases to the cytoplasm. Cells utilize these cellular breakdown products as building blocks for macromolecular synthesis or for sustaining energy homeostasis. As such, autophagy is a major mechanism by which a cell recycles and reallocates nutrients to more essential cellular processes. Autophagy also functions in protein and organelle quality control by degrading damaged or old cellular components such as depolarized mitochondria and unfolded proteins. Protein and organelle turnover through autophagy is critical to prevent the toxic buildup of old and damaged cellular components to maintain homeostasis.

Autophagy has been emerging as a novel cytoprotective mechanism to increase tumor cell survival under conditions of metabolic stress and hypoxia as well as to escape cell death induced by chemotherapy, radiotherapy, or a targeted therapy. For example, aggressive cancers relay on autophagy to support metabolism to maintain tumor cell survival, particularly in the environment of hypoxia and nutrient depletion. In addition, autophagy produces a small number of dormant tumor cells capacity of resuming cellular proliferation when the stress is removed. Autophagy thereby affords cancer cells with the flexibility to tolerate stress, even therapeutic stress, and resume growth when conditions are more favorable. This process of stress survival, dormancy, and regeneration afforded by autophagy can be a major obstacle to achieving successful cancer treatment. Furthermore, a major aspect of cancer treatment such as, e.g., chemotherapy, targeted therapy, and radiotherapy, is infliction of damage on tumor cells sufficient to kill them by apoptosis, necrosis or alternate forms of cell death. In addition to the inherent metabolic stress in the tumor microenvironment, there treatments amplify cellular stress and initiate autophagy. As such, autophagy allows prolonged survival of tumor cells by providing a protective function to limit tumor necrosis and inflammation, and to mitigate genome damage in tumor cells in response to metabolic stress and therapy-induced apoptosis.

As autophagy is a survival pathway used by tumor cells to tolerate metabolic stress, autophagy inhibitors are expected to be useful for cancer therapy. Autophagy inhibitors are particularly attractive because they can target those tumor cells in hypoxic tumor regions, which are therapy, particularly radiation, resistant. Additionally, tumor cells in the process of metastasizing may be particularly dependent on autophagy, supporting approaches to abrogate autophagy in early progression and the adjuvant setting. A particularly useful cancer therapy would be the use of agents that inhibit autophagic degradation to enhance the efficacy of conventional chemotherapeutics, which generally activate the autophagy pathway. The addition of autophagy inhibitors would be expected to enhance cytotoxicity of these agents. For example, treatment with an autophagy inhibitor might increase the efficacy of apoptosis-inducing chemotherapeutics in human patients with cancer. Thus, a cancer therapy directed at blocking autophagy-mediated survival with autophagy inhibitors may be extremely valuable.

Although identifying key inhibitors of autophagy is highly desirable, agents that specifically target the autophagy pathway are currently lacking. The present specification provides autophagy inhibitors that in combination with a chemotherapeutic compound or radiation that induce autophagy result in a synergistically beneficial effect in the treatment of a braod spectrum of cancers.

SUMMARY

Thus, aspects of the present specification disclose a thioxanthone-based autophagy inhibitor. Useful thioxanthone-based autophagy inhibitors include, without limitation, 1-((2-(Diethylamino)ethyl)amino)-4-methylthioxanthen-9-one, 1-(2-diethylaminoethylamino)-4-(hydroxymethyl)-9-thioxanthenone, N-[[1-[[2-(diethylamino)ethyl]amino]-9-oxo-9H-thiaxanthen-4-yl]methyl]methanesulfonamide, indazole analogues thereof, or salts thereof.

Other aspects of the present specification disclose a cancer therapeutic autophagy inducing compound. Non-limiting examples of such compounds include arsenic trioxide, etoposide, rapamycin, histone deacetylase inhibitors, tyrosine kinase inhibitors, tamoxifen, temozolomide, imatinib, bortezomib histone deacetylase inhibitor. Useful histone deacetylase inhibitors include, without limitation, a hydroxamate-type histone deacetylase inhibitor or a benzamide-type histone deacetylase inhibitor. Non-limiting examples of such inhibitors include (2E,4E,6R)-7-(4-dimethylaminophenyl)-N-hydroxy-4,6-dimethyl-7-oxohepta-2,4-dienamide, N-hydroxy-N'-phenyloctanediamide, 4-Dimethylamino-N-(6-hydroxycarbamoylhexyl)-benzamide, N-hydroxy-3-[(E)-3-(hydroxyamino)-3-oxoprop-1-enyl]benzamide, (2E)-3-[3-(anilinosulfonyl)phenyl]-N-hydroxyacrylamide, ((E)-N-hydroxy-3-[4-[[2-hydroxyethyl-[2-(1H-indol-3-ylethyl]amino]methyl]phenyl]prop-2-enamide, (E)-N-hydroxy-3-[4-[[2-(2-methyl-1H-indol-3-yl)ethylamino]methyl]phenyl]prop-2-enamide, N-(2-aminophenyl)-N'-phenyl-octanediamide, 4-(2-aminophenylcarbamoyl)benzylcarbamate, 4-acetamido-N-(2-aminophenyl)benzamide, N-(2-aminophenyl)-4-[[(4-pyridin-3-ylpyrimidin-2-yl)amino]methyl]benzamide, 3-(dimethylaminomethyl)-N-[2-[4-(hydroxycarbamoyl)phenoxy]ethyl]-1-benzofuran-2-carboxamide, or {6-[(diethylamino)methyl]-2-naphthyl}methyl {4-[(hydroxyamino)carbonyl]phenyl}carbamate, or salts thereof.

Other aspects of the present specification disclose a pharmaceutical composition comprising a compound or compounds disclosed herein. In one aspect, a pharmaceutical composition comprises a therapeutically effective amount of a thioxanthone-based autophagy inhibitor. In another aspect, a pharmaceutical composition comprises a therapeutically effective amount of a cancer therapeutic autophagy inducing compound. In yet another aspect, a pharmaceutical composition comprises a therapeutically effective amount of a thioxanthone-based autophagy inhibitor; and a therapeutically effective amount of a cancer therapeutic autophagy inducing compound. The pharmaceutical composition disclosed herein may further comprise a pharmaceutically acceptable carrier.

Yet other aspects of the present specification disclose a use of a compound or compounds disclosed herein or a composition disclosed herein for the manufacture of a medicament to treat cancer.

Still other aspects of the present specification disclose a method of treating cancer, the method comprising administering an effective amount of a thioxanthone-based autophagy inhibitor disclosed herein to a mammal in need thereof; and administering an effective amount of a cancer therapeutic autophagy inducing compound disclosed herein to a mammal in need thereof; wherein the administration of both the thioxanthone-based autophagy inhibitor and the cancer therapeutic autophagy inducing compound reduces a symptom associated with cancer, thereby treating the cancer. The thioxanthone-based autophagy inhibitor and the cancer therapeutic autophagy inducing compound may be administered concurrently or sequentially. Sequential administration of a thioxanthone-based autophagy inhibitor and the cancer therapeutic autophagy inducing compound may be administered within about three hours of each other, within about two hours of each other, or within about one hour of each other. Non-limiting example of a cancer that can be treated using the compounds, compositions and methods disclosed herein include a lung cancer, a brain cancer, a central nervous system cancer, a breast cancer, a colon cancer, a leukemia, a myeloma, a prostate, or an ovarian cancer. In further aspects, the method further comprises administering a radiotherapy.

Further aspects of the present specification disclose a use of a thioxanthone-based autophagy inhibitor and a cancer therapeutic autophagy inducing compound disclosed herein or a composition comprising such compounds as disclosed herein for the treatment of cancer, wherein the administration of both the thioxanthone-based autophagy inhibitor and the cancer therapeutic autophagy inducing compound reduces a symptom associated with cancer, thereby treating the cancer. Non-limiting example of a cancer that can be treated using the compounds, compositions and methods disclosed herein include a lung cancer, a brain cancer, a central nervous system cancer, a breast cancer, a colon cancer, a leukemia, a myeloma, a prostate, or an ovarian cancer. In yet other aspects, the method further comprises administering radiotherapy.

Yet further aspects of the present specification disclose a pharmaceutical kit comprising a pharmaceutical composition comprising a therapeutically effective amount of a thioxanthone-based autophagy inhibitor and a pharmaceutically acceptable carrier, and a pharmaceutical composition comprising a therapeutically effective amount of a cancer therapeutic autophagy inducing compound and a pharmaceutically acceptable carrier.

Still other aspects of the present specification disclose a method of treating cancer, the method comprising administering an effective amount of a thioxanthone-based autophagy inhibitor disclosed herein to a mammal in need thereof; and administering an effective amount of a radiotherapy disclosed herein to a mammal in need thereof; wherein the administration of both the thioxanthone-based autophagy inhibitor and the radiotherapy reduces a symptom associated with cancer, thereby treating the cancer. The thioxanthone-based autophagy inhibitor and the radiotherapy may be administered concurrently or sequentially. Sequential administration of a thioxanthone-based autophagy inhibitor and the radiotherapy may be administered within about three hours of each other, within about two hours of each other, or within about one hour of each other. Non-limiting example of a cancer that can be treated using the compounds, compositions and methods disclosed herein include a lung cancer, a brain cancer, a central nervous system cancer, a breast cancer, a colon cancer, a leukemia, a myeloma, a prostate, or an ovarian cancer.

Further aspects of the present specification disclose a use of a thioxanthone-based autophagy inhibitor or a composition comprising such a compound and a radiotherapy disclosed herein for the treatment of cancer, wherein the administration of both the thioxanthone-based autophagy inhibitor and the radiotherapy reduces a symptom associated with cancer, thereby treating the cancer. Non-limiting example of a cancer that can be treated using the compounds, compositions and methods disclosed herein include a lung cancer, a brain cancer, a central nervous system cancer, a breast cancer, a colon cancer, a leukemia, a myeloma, a prostate, or an ovarian cancer.

BRIEF DESCRIPTION OF THE DRAWINGS

FIG. 2. Lucanthone and Chloroquine treatment decrease cell viability.

FIG. 3. Cathepsin D expression is highly elevated following Lucanthone treatment.

FIG. 5. Lucanthone induces cathepsin D expression and decreases cell viability independently of p53.

FIG. 6. Lucanthone enhances the anticancer activity of Vorinostat.

FIG. 7. Lucanthone enhances the anticancer activity of Belinostat.

DESCRIPTION

Figure 1A:
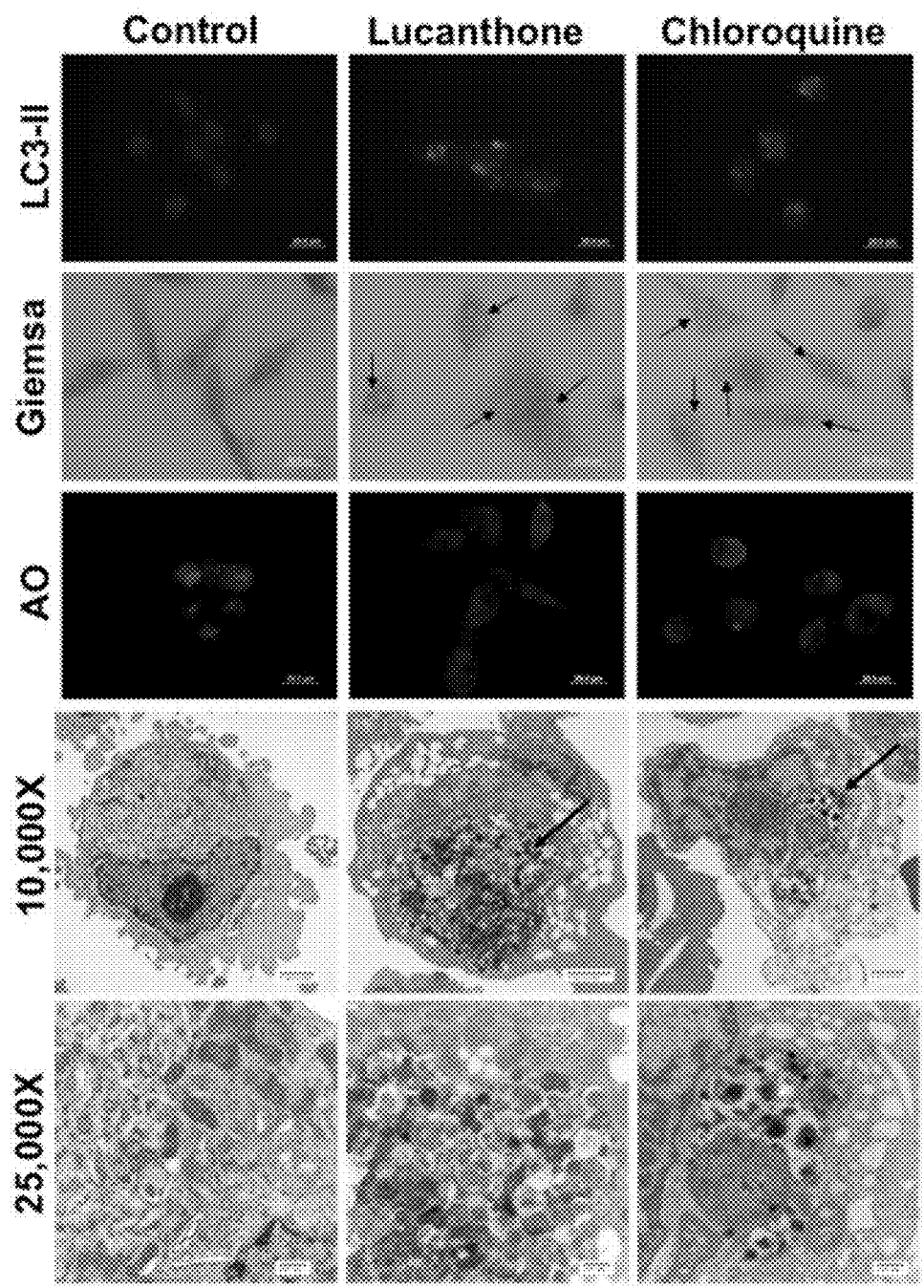
FIG. 1A. Lucanthone induction of LC3-II formation, vacuolization, and LMP. LC3-II was visualized by immunocytochemistry, vacuolization (arrows) by Giemsa staining, and lysosomal membrane permeabilization by loss of acridine orange fluorescence. Electron microscopy demonstrates vacuolization and electron dense particle accumulation (arrows), which suggests undegraded protein accumulation.
Figure 1B:
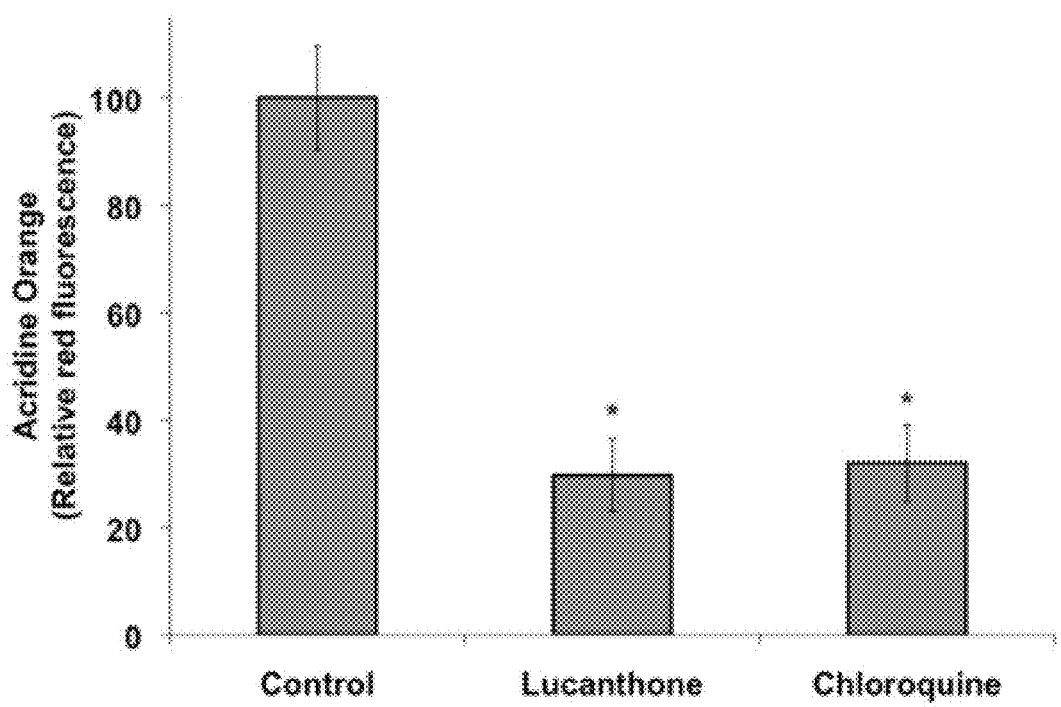
FIG. 1B. Quantification of lysosomal membrane permeabilization. Mean±standard deviation, n=5. *Indicates a significant difference from the controls. $P<0.05$.
Figure 1C:
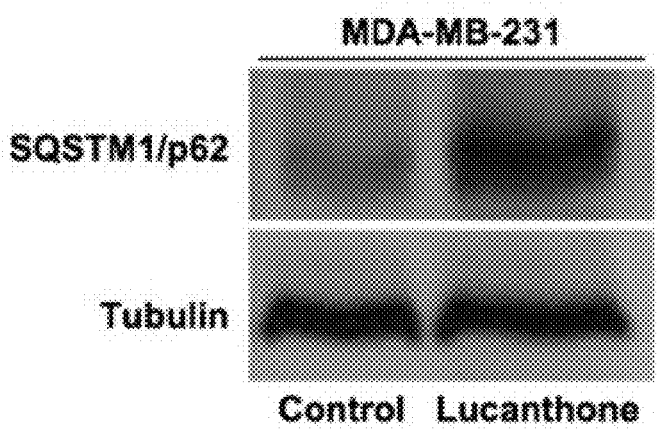
FIG. 1C. Lucanthone stimulates SQSTM1/p62 accumulation.
Figure 1D:
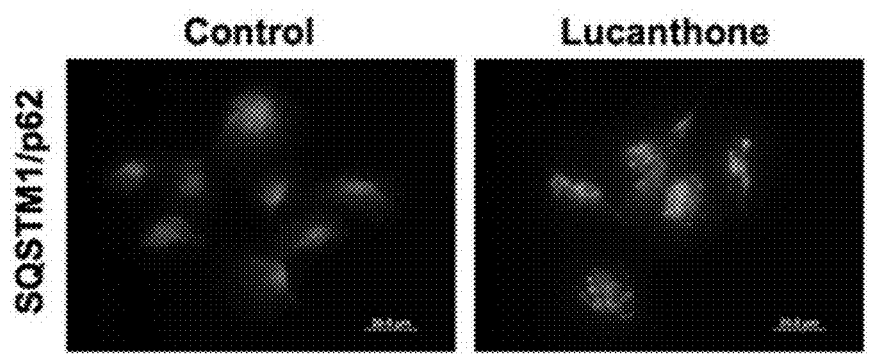
FIG. 1D. Lucanthone stimulates SQSTM1/p62 aggregation as shown visually by fluorescence microscopy (FIG. 1D) and by quantification of relative fluorescence (FIG. 1E).
Figure 1E:
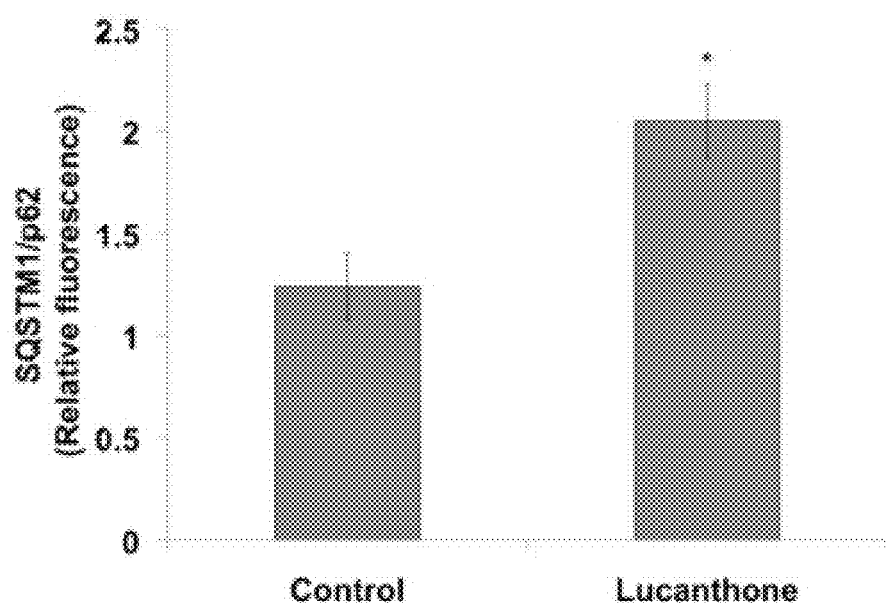
FIG. 1. Lucanthone inhibits autophagy.
FIG. 1F. Lucanthone, Bafilomycin A1, and the combination induce LC3-II formation and SQSTM1/p62 accumulation.
FIG. 1G. Lucanthone, Bafilomycin A1, and the combination induce apoptosis in breast cancer cell lines.
Figure 1F:
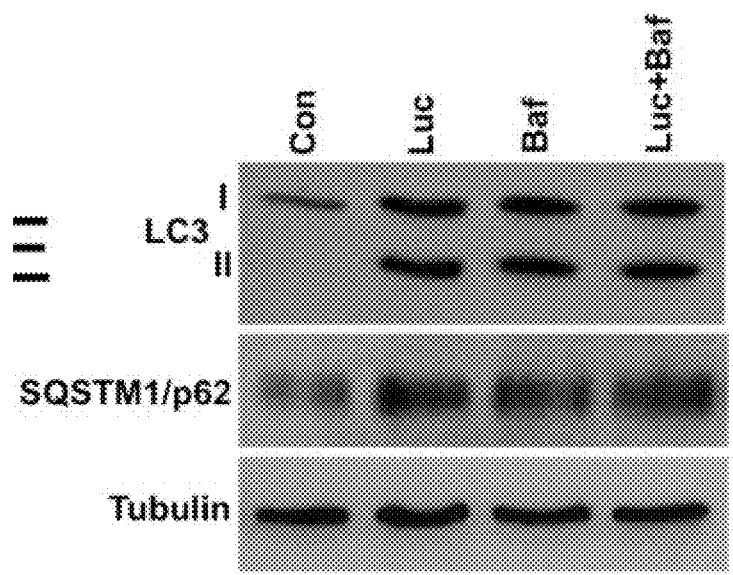
Figure 1G:
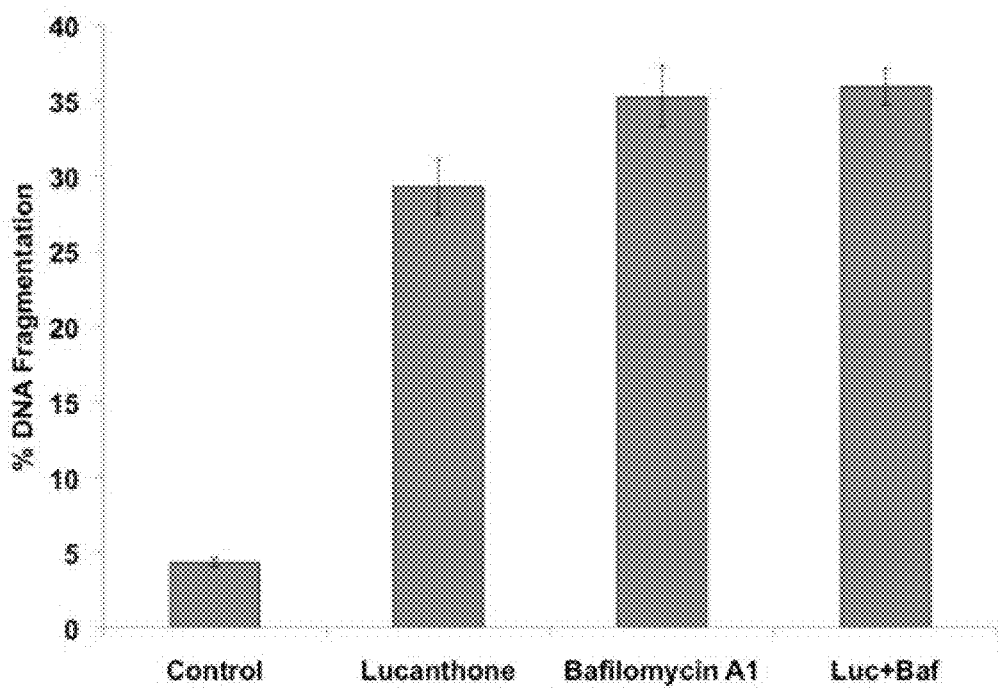

As uncontrolled cell growth is the underlying cause of all cancers, compounds, compositions, and methods that can reduce or prevent this uncontrolled cell growth would be an effective treatment for cancer. The present specification discloses compounds, compositions, and methods that can reduce or prevent the uncontrolled cell growth displayed by cancer cells. The compounds comprise, in part, a thioxanthone-based autophagy inhibitor (TAPI) and a cancer therapeutic autophagy inducing compound (CTAPIC). TAPIs inhibit the autophagy-mediated survival of tumor cells, making them more susceptible to metabolic stress, hypoxia and cancer treatments, such as, e.g., chemotherapy, radiotherapy, or targeted therapies like immunotherapy, hormonal therapy, or angiogenesis inhibitor therapy. CTAPICs are conventional chemotherapeutic or targeted therapeutic agents that as a consequence of their mechanism of action induce autophagy. Surprisingly, although a TAPI and CTAPIC have opposite effects on tumor cells, it was discovered that a combination of TAPI and HDACI compounds provide a synergistic effect that greatly improves the therapeutically beneficial result and provides a more effective cancer treatment. As a corollary to this finding, a combined treatment of a TAPI and a radiation therapy would also produce a synergistically beneficial cancer treatment because radiation therapy also induces autophagy.

Aspects of the present specification disclose, in part, a thioxanthone-based autophagy inhibitor (TAPI). As demonstrated in the Examples section, a TAPI inhibits autophagy, disrupts lysosome function, induces cathepsin D expression, is cytotoxic to cancer cells, has an anticancer activity that is independent of p53 status, and enhances the anticancer activity of CTAPICs. A TAPI useful in the methods disclosed herein include any thioxanthone-based compound having attached short chains that appear similar to the deoxyribose sugar ring without a base attached and phosphodiester bond. Non-limiting examples of a TAPI include Lucanthone (Miracil D), 1-((2-(Diethylamino)ethyl)amino)-4-methylthioxanthen-9-one, Hycanthone 1-(2-diethylaminoethylamino)-4-(hydroxymethyl)-9-thioxanthenone, indazole analogues of Lucanthone and Hycanthone, (WIN33377) N-[[1-[[2-(diethylamino)ethyl]amino]-9-oxo-9H-thiaxanthen-4-yl]methyl]meth anesulfonamide, together with physiologically tolerated derivatives, analogs, and salts thereof. Other thioxanthone apurinic/apyrimidinic endonuclease inhibitors are described in, e.g., Thomas Corbett, et al., *Antitumor Activity of N-[[1-[[2-(diethylamino)ethyl]amino]-9-oxo-9H-thiaxanthen-4-yl]methyl]meth anesulfonamide (WIN33377) and Analogues*, Exp. Opin. Invest. Drugs 3: 1281-1292 (1994); and Mark P. Wentland, et al., *Anti-solid Tumor Efficacy and Preparation of N-[[1-[[2-(diethylamino)ethyl]amino]-9-oxo-9H-thiaxanthen-4-yl]methyl]methanesulfonamide (WIN33377) and Related Derivatives*, Bioorg. Med. Chem. Lett. 4: 609-614 (1994); each of which is incorporated by reference in its entirety.

In aspects of this embodiment, a TAPI is 1-((2-(Diethylamino)ethyl)amino)-4-methylthioxanthen-9-one, 1-(2-diethylaminoethylamino)-4-(hydroxymethyl)-9-thioxanthenone, or N-[[1-[[2-(diethylamino)ethyl]amino]-9-oxo-9H-thiaxanthen-4-yl]methyl]meth anesulfonamide. The chemical structure of these compounds is shown below.

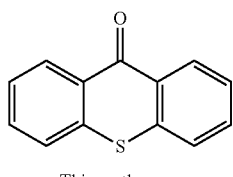

Thioxanthenone

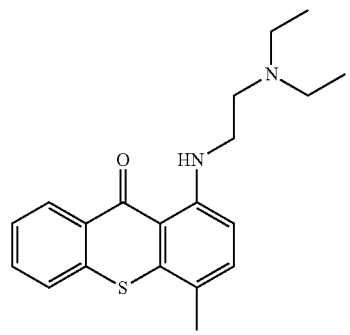

Lucanthone (Miracil D)

1-((2-(Diethylamino)ethyl)amino)-4-methylthioxanthen-9-one

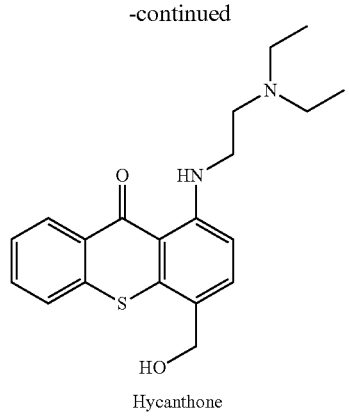

Hycanthone 1-(2-diethylaminoethylamino)-4-(hydroxymethyl)-9-thioxanthenone

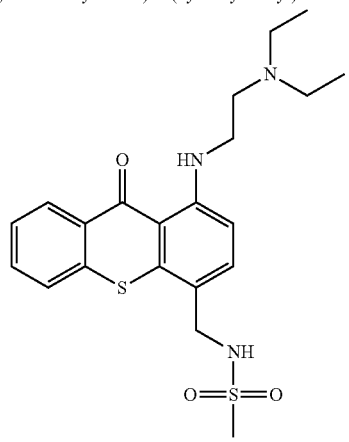

WIN-33377 (SR-233377)

N-[[1-[[2-(diethylamino)ethyl]amino]-9-oxo-9H-thiaxanthen-4-yl]methyl]meth anesulfonamide Aspects of the present specification disclose, in part, a cancer therapeutic autophagy inducing compound. A cancer therapeutic autophagy inducing compound (CTAPIC) is a class of anticancer compounds useful in treating a broad spectrum of cancers that nonetheless induce autophagy, and thereby inhibit apoptosis. Many cancer therapeutics induce autophagy because they induce damage (cytotoxic chemotherapy), metabolic stress (angiogenesis inhibitors, 2-deoxyglucose), or block growth signaling pathways (targeted non-cytotoxics, kinase inhibitors) by mimicking factor deprivation or starvation. As such, a CTAPIC includes chemotherapeutic and targeted therapeutic compounds like immunotherapeutic, hormonal therapeutic, or angiogenesis inhibitor compounds. Non-limiting examples of such compounds include anti-angiogenesis compounds, tyrosine kinase inhibitors, vascular endothelial growth factor receptor (VEGFR) inhibitors, histone deacetylase inhibitors, Farnesyltransferase inhibitors, mTOR inhibitors, glycolysis inhibitors, and vitamin D analogues and retinoids compounds. Other CTAPICs include, without limitation, arsenic trioxide, Bevacizumab carboplatin I/II, Bortezomib, deoxyglucose, Docetaxel, Endostatin, etoposide, Everolimus, Gefitinib, imatinib, ixabepilone, LonaFarnib, rapamycin, sunitinib malate, tamoxifen, temozolomide, and Temsirolimus.

Aspects of the present specification disclose, in part, a histone deacetylase inhibitor. Histone deacetylase inhibitors (HDAC inhibitors, HDACI, or HDI) are a class of compounds that interfere with the function of HDACs and can result in hyperacetylation of histones, thereby affecting gene expression. HDAC inhibitors are classified according to their chemical structures and are endowed with different specificity and affinity for the HDACs of classes 1, 2, and 4. Among HDAC inhibitors, the most potent are the hydroxamate-type (hydroxamic acid-type) HDAC inhibitors that exhibit a dose-dependent antitumor activity against breast cancer and have been recently approved as a therapeutic for cutaneous T-cell lymphomas. Non-limiting examples of hydroxamate-type HDAC inhibitors include Trichostatin A, Vorinostat, M-344, CBHA, Belinostat, Dacinostat, and Panobinostat. Another important class of clinically effective HDAC inhibitors is the benzamide-type HDAC inhibitors which demonstrated low toxicity and activity in solid and haematological neoplasms. Non-limiting examples of benzamide-type HDAC inhibitors include Entinostat, Tacedinaline, and Mocetinostat. Other classes of HDAC inhibitors are short chain fatty acids (SCFA) such as, e.g., phenylbutyrate, valproic acid, and similar aliphatic acid compounds; epoxyketone and non-epoxyketone containing cyclic tetrapeptides such as, e.g., trapoxin B and depsipeptides; electrophilic ketones, and hybrid molecules. SOFA, although widely used (especially valproic acid) and clinically efficacious, have weak HDAC inhibition constants. The sirtuin Class III HDACs are dependent on NAD+ and are, therefore, inhibited by nicotinamide, as well derivatives of NAD, dihydrocoumarin, naphthopyranone, and 2-hydroxynaphaldehydes. HDAC inhibitors are also potent radiation sensitizers.

Epigenetic modifications are reversible chromatin rearrangements that in normal cells modulate transcriptional expression of genes, without changing DNA sequence. Transcription is one of the steps involved in the production of proteins from DNA. In order for transcription to occur, transcription factors have to bind to specific binding sites on the DNA. When the DNA is in its condensed form, it is difficult for transcription factors to physically gain access to their cognate binding sites, with the end result that occurs infrequently.

Histones are proteins that play a central role in the transcriptional regulation of genes. These globular proteins have a flexible N-terminus that is normally positively charged due to amine groups present on lysine and arginine residues. These positive charges help the N-terminus portion of histones to interact with and bind to the negatively charged phosphate groups on the DNA backbone. It is this histone-DNA interaction that helps condense DNA into its compact chromatin form as chromosomes. Thus, by ensuring that DNA is bundled in its condensed form, histones play a major role in restricting the binding of transcription factors to DNA.

The binding of histones to DNA is controlled by various enzymes present in the cell. Under conditions where transcription of a certain gene is supported, enzymes known as histone acetyltransferases (HATs), or lysine deacetylases (KDAC), add acetyl groups to E-N-acetyl lysine residues on histones. Acetylation neutralizes the positive charges on the N-terminus region of histones, with the consequence that the acetylated histones are no longer able to interact with the DNA backbone. This decreased binding allows chromatin expansion (or chromatin decondensation), permitting gene transcription to take place because transcription factors can now access their DNA binding sites and activate gene transcription. Under conditions where transcription of a gene is no longer supported, enzymes known as histone deacetylases (HDACs) remove the acetyl group added by the HATs. Deacetylation increases the positive charge of the N-terminus of histones thereby encouraging high-affinity binding between the histones and the DNA backbone. The resulting chromatin condensation prevents gene transcription because transcription factors are physically blocked from interacting with their DNA binding sites. Thus, HATs facilitate chromatin decondensation, and as such promote gene transcription, whereas HDACs facilitate chromatin condensation, and as such suppress gene transcription.

There are 18 known human HDACs, grouped into four classes based on function and DNA sequence similarity of their accessory domains. The first two classes are considered "classical" HDACs whose activities are inhibited by trichostatin A (TSA), whereas the third group is a family of NAD+-dependent proteins not affected by TSA. The fourth class is considered an atypical category based solely on DNA sequence dissimilarity to the others. Class I includes HDAC1, HDAC2, HDAC3, and HDAC8 and have homology to yeast reduced potassium dependency 3 (RPD3). HDAC4, HDAC5, HDAC7, and HDAC9 belong to class II and have homology to yeast histone deacetylase 1 (HDA1). HDAC6 and HDAC10 contain two catalytic sites and are classified as class IIa. Class III, also known as the sirtuins are related to the SIR2 and include SIRT1-7, whereas HDAC11 is placed in class IV because it has conserved residues in its catalytic center that are shared by both class I and class II HDACs.

Several antineoplastic compounds are known to act as HDAC inhibitors. As such, it is believed that inhibition of chromatin condensation could provide a therapeutically beneficial effect in the treatment of cancer because such chromatin remodeling results in 1) transcriptional suppression of key apoptosis and cell cycle regulatory genes, which thereby promote cell cycle arrest and apoptosis; 2) increased tumor suppressor heterozygousity, and/or 3) inhibition of angiogenesis. Thus, the epigenetic regulation of gene transcription through chromatin condensation has emerged as an important mechanism that leads to tumorogenesis.

In aspects of this embodiment, a histone deacetylase inhibitor is a hydroxamate-type histone deacetylase or a benzamide-type histone deacetylase. In other aspects of this embodiment, a histone deacetylase inhibitor is (2E,4E,6R)-7-(4-dimethylaminophenyl)-N-hydroxy-4,6-dimethyl-7-oxohepta-2,4-dienamide, N-hydroxy-N'-phenyloctanediamide, 4-Dimethylamino-N-(6-hydroxycarbamoylhexyl)-benzamide, N-hydroxy-3-[(E)-3-(hydroxyamino)-3-oxoprop-1-enyl]benzamide, (2E)-3-[3-(anilinosulfonyl)phenyl]-N-hydroxyacrylamide, ((E)-N-hydroxy-3-[4-[[2-hydroxyethyl-[2-(1H-indol-3-yl)ethyl]amino]methyl] phenyl]prop-2-enamide, (E)-N-hydroxy-3-[4-[[2-(2-methyl-1H-indol-3-yl)ethylamino]methyl]phenyl]prop-2-enamide, N-(2-aminophenyl)-N'-phenyl-octanediamide, 4-(2-aminophenylcarbamoyl)benzylcarbamate, 4-acetamido-N-(2-aminophenyl)benzamide, N-(2-aminophenyl)-4-[[(4-pyridin-3-ylpyrimidin-2-yl)amino]methyl]benzamide, 3-(dimethylaminomethyl)-N-[2-[4-(hydroxycarbamoyl) phenoxy]ethyl]-1-benzofuran-2-carboxamide, or {6-[(diethylamino)methyl]-2-naphthyl}methyl {4-[(hydroxyamino)carbonyl]phenyl}carbamate. The chemical structure of these inhibitors is shown below.

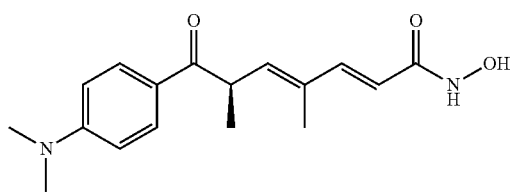

Trichostatin A (2E,4E,6R)-7-(4-dimethylaminophenyl)-N-hydroxy-4,6-dimethyl-7-oxohepta-2,4-dienamide

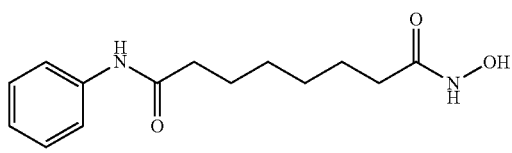

Vorinostat (SAHA, Zolinza)

N-hydroxy-N'-phenyloctanediamide

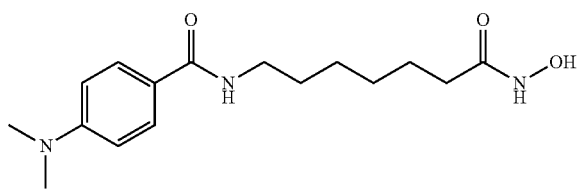

M-344 (D-237)

4-Dimethylamino-N-(6-hydroxycarbamoylhexyl)-benzamide

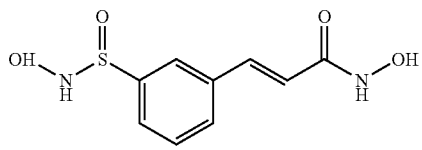

CBHA

N-hydroxy-3-[(E)-3-(hydroxyamino)-3-oxoprop-1-enyl]benzamide

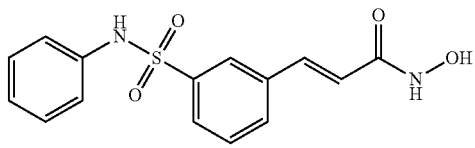

Belinostat (PXD-101, PX-105684)

(2E)-3-[3-(anilinosulfonyl)phenyl]-N-hydroxyacrylamide

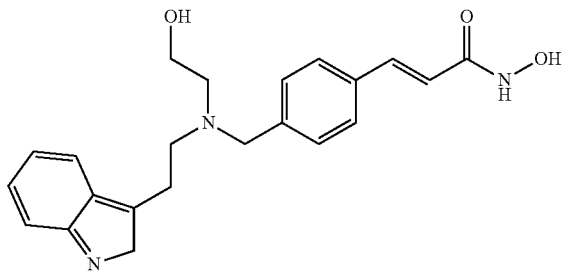

Dacinostat (LAQ-824, NVP-LAQ824,)

((E)-N-hydroxy-3-[4-[[2-hydroxyethyl-[2-(1H-indol-3-yl)ethyl]amino]methyl]phenyl]prop-2-enamide

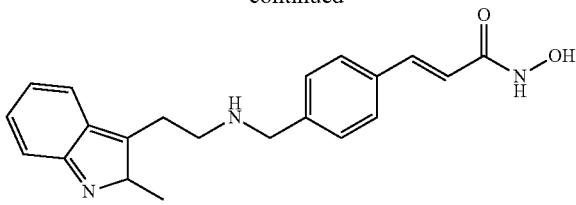

Panobinostat (LBH-589, NVP-LBH589)

((E)-N-hydroxy-3-[4-[[2-(2-methyl-1H-indol-3-yl)ethylamino]methyl]phenyl]prop-2-enamide

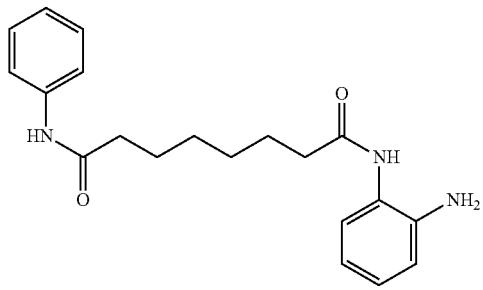

BML-210

N-(2-aminophenyl)-N'-phenyl-octanediamide

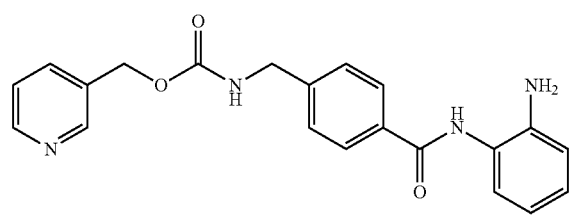

Entinostat (MS-275, SNDX-275, MS-27-275)

4-(2-aminophenylcarbamoyl)benzylcarbamate

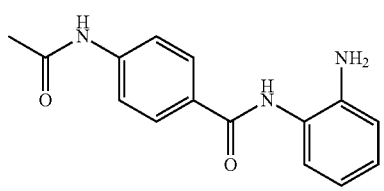

Tacedinaline (Cl-994, PD-123654, GOE-5549)

4-acetamido-N-(2-aminophenyl)benzamide)

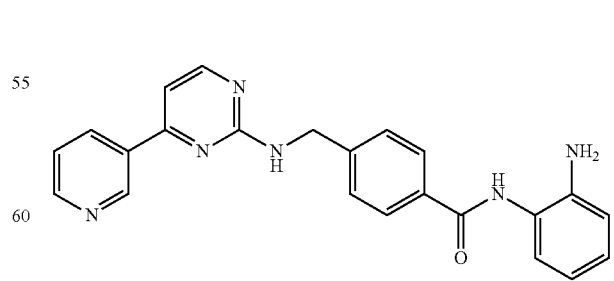

Mocetinostat (MGCD-0103)

N-(2-aminophenyl)-4-[[(4-pyridin-3-ylpyrimidin-2-yl)amino]methyl]benzamide

-continued

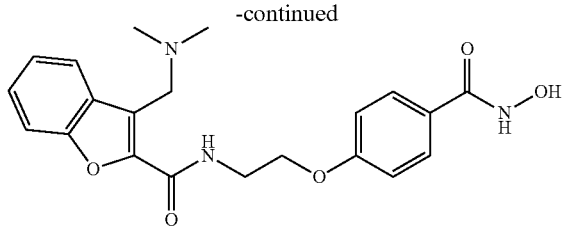

PCI-24781

3-(dimethylaminomethyl)-N-[2-[4-(hydroxycarbamoyl)phenoxy]ethyl]-1-benzofuran-2-carboxamide

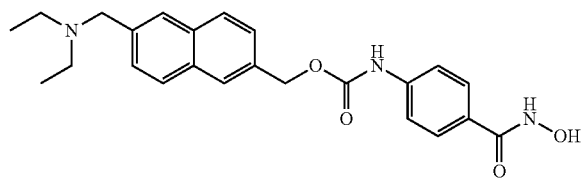

ITF-2357

{6-[(diethylamino)methyl]-2-naphthyl}methyl {4-[(hydroxyamino)carbonyl]phenyl}carbamate Aspects of the present specification, disclose, in part, a targeted therapeutic. A targeted therapeutic compound, includes, without limitation, an immunotherapeutic, a hormonal therapeutic, and an angiogenesis inhibitor compound. Hormonal therapy involves the manipulation of the endocrine system through exogenous administration of specific hormones, particularly steroid hormones, or drugs which inhibit the production or activity of such hormones (hormone antagonists). Because steroid hormones are powerful drivers of gene expression in certain cancer cells, changing the levels or activity of certain hormones can cause certain cancers to cease growing, or even undergo cell death. Surgical removal of endocrine organs, such as orchidectomy and oophorectomy can also be employed as a form of hormonal therapy.

Immunotherapies are treatments that use natural body substances or drugs made from natural body substances. They stimulate the body to attack cancer cells and overcome side effects caused by other cancer treatments. Immunotherapies use the immune system to reject cancer. The main premise is stimulating the patient's immune system to attack the malignant tumor cells that are responsible for the disease. This can be either through immunization of the patient, in which case the patient's own immune system is trained to recognize tumor cells as targets to be destroyed, or through the administration of therapeutic antibodies as drugs, in which case the patient's immune system is recruited to destroy tumor cells by the therapeutic antibodies.

The compositions disclosed herein may, or may not, comprise any number and combination of thioxanthone-based autophagy inhibitors and cancer therapeutic autophagy inducing compounds disclosed herein. For instance, a composition can comprise, e.g., two or more thioxanthone-based autophagy inhibitors and/or cancer therapeutic autophagy inducing compounds, three or more thioxanthone-based autophagy inhibitors and/or cancer therapeutic autophagy inducing compounds, four or more thioxanthone-based autophagy inhibitors and/or cancer therapeutic autophagy inducing compounds, or five or more thioxanthone-based autophagy inhibitors and/or cancer therapeutic autophagy inducing compounds.

A thioxanthone-based autophagy inhibitor and a cancer therapeutic autophagy inducing compound disclosed herein, or a composition comprising such a compound or compounds is generally administered to an individual as a pharmaceutical composition. Pharmaceutical compositions may be prepared by combining a therapeutically effective amount of at least one compound as disclosed herein, or a pharmaceutically acceptable acid addition salt thereof, as an active ingredient, with conventional acceptable pharmaceutical excipients, and by preparation of unit dosage forms suitable for therapeutic use. As used herein, the term "pharmaceutical composition" and refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

Liquid dosage forms suitable for parenteral injection may comprise physiologically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. In liquid formulations, a therapeutically effective amount typically is between about 0.0001% (w/v) to about 50% (w/v), preferably about 0.001% (w/v) to about 1.0% (w/v).

Solid dosage forms suitable for oral administration include capsules, tablets, pills, powders and granules. In such solid dosage forms, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents. In solid formulations, a therapeutically effective amount typically is between about 0.001 mg/kg to about 100 mg/kg, preferably about 0.1 mg/kg to about 10 mg/kg.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

A thioxanthone-based autophagy inhibitor and a cancer therapeutic autophagy inducing compound disclosed herein may also be incorporated into a drug delivery platform in order to achieve a controlled compound release profile over time. Such a drug delivery platform comprises a compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present specification disclose, in part, a pharmaceutical kit including a pharmaceutical composition comprising a therapeutically effective amount of a thioxanthone-based autophagy inhibitor and a pharmaceutically acceptable carrier, and a pharmaceutical composition comprising a therapeutically effective amount of a cancer therapeutic autophagy inducing compound and a pharmaceutically acceptable carrier.

Aspects of the present invention provide, in part, a cancer. The thioxanthone-based autophagy inhibitors, cancer therapeutic autophagy inducing compounds, compositions comprising such compounds, and methods disclosed herein can be useful to treat any cancer. Cancer is a group of more than 100 diseases in which a group of cells display uncontrolled proliferation in a mammalian body, and as such is fundamentally a disease that affects the regulatory mechanism the body uses to control cell division and growth. In most cases, cancer cells form a clump of cells called a tumor, although in some cancers, like leukemia, the cells do not form tumors. Tumors may be malignant or benign. Besides, malignant tumors (or cancers) comprise cells with abnormal genetic material and usually undergo rapid uncontrolled cell growth, invade and destroy adjacent tissue, and sometimes spread to other locations in the body via lymph or blood (i.e., metastasis). Cancer is associated with a high incidence of mortality because if the invasion and metastasis of the cancer cells throughout the body are not stopped, cancer cells will invade vital organs and lead to the dysfunction of the organs and eventual death. The malignant properties of cancers differentiate them from benign tumors, which are usually slow-growing and self-limited, do not invade or metastasize, and as such, are generally not life-threatening. Cancers at the local, regional or distant stage are considered invasive. A very early cancer found in only a few layers of cells, called in situ cancer, is considered non-invasive.

Cancer is a diverse class of diseases which differ widely in their causes and biology. Cancers are caused by a variety of factors working alone or in combination. Some cancers are caused by external factors such as tobacco, diet, certain chemicals, radiation, and viruses. Other cancers are caused by internal factors such as hormones, immune conditions, and inherited genetic mutations. Usually ten or more years pass between exposure to a factor that causes cancer and detectable disease.

Cancers are generally classified by the type of cell that resembles the tumor and, therefore, the tissue presumed to be the origin of the tumor. Carcinomas are malignant tumors derived from epithelial cells. This group represents the most common cancers, including the common forms of a lung cancer, a brain cancer, a central nervous system cancer, a breast cancer, a colon cancer, a leukemia, a myeloma, a prostate and an ovarian cancer. Sarcomas are malignant tumors derived from connective tissue, or mesenchymal cells. Blastomas are usually malignant tumors which resembles an immature or embryonic tissue. Many of these tumors are most common in children. Lymphomas and leukemias are malignancies derived from hematopoietic (blood-forming) cells. Lastly, germ cell tumors are tumors derived from totipotent cells. In adults most often found in the testicle and ovary; in fetuses, babies, and young children most often found on the body midline, particularly at the tip of the tailbone. As such, as used herein, the term "cancer" includes a primary cancer and a metastatic cancer that can be a carcinoma, a sarcoma, a lymphoma, a leukemia, a blastoma, or a germ cell tumor.

Aspects of the present invention provide, in part, reducing a symptom associated with cancer. In an aspect of this embodiment, the symptom reduced is an increase in the growth rate of cancer cells. In another aspect of this embodiment, the symptom reduced is an increase in the cell division rate of cancer cells. In yet another aspect of this embodiment, the symptom reduced is an increase in the extent of invasion of cancer cells into adjacent tissue or organs. In still another aspect of this embodiment, the symptom reduced is an increase in the extent of metastasis. In a further aspect of this embodiment, the symptom reduced is an increase in angiogenesis. In a yet further aspect of this embodiment, the symptom reduced is a decrease in apoptosis. In a still further aspect of this embodiment, the symptom reduced is a decrease in cell death or cell necrosis. Thus, a treatment using the compounds, compositions, and methods disclosed herein will decrease the growth rate of cancer cells, decrease the cell division rate of cancer cells, decrease the extent of invasion of cancer cells into adjacent tissue or organs, decrease the extent of metastasis, decrease angiogenesis, increase apoptosis, and/or increase cell death and/or cell necrosis.

Aspects of the present invention provide, in part, a mammal. A mammal includes a human, and a human can be a patient. Other aspects of the present invention provide, in part, an individual. An individual includes a mammal and a human, and a human can be a patient.

Aspects of the present invention provide, in part, administering a composition comprising a compound or compounds disclosed herein. As used herein, the term "administering" means any delivery mechanism that provides a composition comprising a compound or compounds disclosed herein to an individual that potentially results in a clinically, therapeutically, or experimentally beneficial result.

A composition comprising a compound or compounds disclosed herein can be administered concurrently or sequentially. As such, composition comprising a thioxanthone-based autophagy inhibitor can be administered at the same time as a composition comprising a cancer therapeutic autophagy inducing compound (concurrently) or sequentially in any order at different points in time. Also, concurrently as used may mean that a thioxanthone-based autophagy inhibitor and cancer therapeutic autophagy inducing compound may be taken together at the same time as part one pharmaceutical composition or together at the same time but in separate pharmaceutical compositions. Thus, each component can be administered separately but sufficiently closely in time so as to provide the desired therapeutic effect. Alternatively, the administration of a thioxanthone-based autophagy inhibitor and a cancer therapeutic autophagy inducing compound can be within about one hour of each other, within about two hours of each other, or within about three hours of each other.

A composition comprising a compound or compounds disclosed herein can be administered for one or more cycles. In one embodiment, one cycle comprises seven times once every four days.

Administration of a composition comprising a compound or compounds disclosed herein include a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A composition comprising a compound or compounds disclosed herein can be administered to a mammal using a variety of routes. Routes of administration suitable for a method of treating a cancer as disclosed herein include both local and systemic administration. Local administration results in significantly more delivery of a composition to a specific location as compared to the entire body of the mammal, whereas, systemic administration results in delivery of a composition to essentially the entire body of the individual. Routes of administration suitable for a method of treating a cancer as disclosed herein also include both central and peripheral administration. Central administration results in delivery of a composition to essentially the central nervous system of the individual and includes, e.g., intrathecal administration, epidural administration as well as a cranial injection or implant. Peripheral administration results in delivery of a composition to essentially any area of an individual outside of the central nervous system and encompasses any route of administration other than direct administration to the spine or brain. The actual route of administration of a composition comprising a compound or compounds disclosed herein used in a mammal can be determined by a person of ordinary skill in the art by taking into account factors, including, without limitation, the type of cancer, the location of the cancer, the cause of the cancer, the severity of the cancer, the degree of relief desired, the duration of relief desired, the particular compound or compounds used, the rate of excretion of the compound or compounds used, the pharmacodynamics of the compound or compounds used, the nature of the other compounds to be included in the composition, the particular route of administration, the particular characteristics, history and risk factors of the individual, such as, e.g., age, weight, general health and the like, or any combination thereof.

In an embodiment, a composition comprising a compound or compounds disclosed herein is administered systemically to a mammal. In another embodiment, a composition comprising a compound or compounds disclosed herein is administered locally to a mammal. In an aspect of this embodiment, a composition comprising a compound or compounds disclosed herein is administered to a tumor of a mammal. In another aspect of this embodiment, a composition comprising a compound or compounds disclosed herein is administered to the area surrounding a tumor of a mammal.

Aspects of the present invention provide, in part, administering a therapeutically effective amount of a composition comprising a compound or compounds disclosed herein. As used herein, the term "therapeutically effective amount" is synonymous with "therapeutically effective dose" and when used in reference to treating a cancer means the minimum dose of a a compound or compounds disclosed herein necessary to achieve the desired therapeutic effect and includes a dose sufficient to reduce a symptom associated with a cancer. In aspects of this embodiment, a therapeutically effective amount of a composition comprising a compound or compounds disclosed herein reduces a symptom associated with a cancer by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a composition comprising a compound or compounds disclosed herein reduces a symptom associated with a cancer by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a composition comprising a compound or compounds disclosed herein reduces a symptom associated with a cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a compound or compounds disclosed herein is the dosage sufficient to reduces a symptom associated with a cancer for, e.g., at least one week, at least one month, at least two months, at least three months, at least four months, at least five months, at least six months, at least seven months, at least eight months, at least nine months, at least ten months, at least eleven months, or at least twelve months.

The amount of active component in the composition and method for treating cancer can be varied so that a suitable dosage is obtained. The actual therapeutically effective amount of a composition comprising a compound or compounds disclosed herein to be administered to a mammal can be determined by a person of ordinary skill in the art by taking into account factors, including, without limitation, the type of cancer, the location of the cancer, the cause of the cancer, the severity of the cancer, the duration of treatment, the degree of relief desired, the duration of relief desired, the particular compound or compounds used, the rate of excretion of the compound or compounds used, the pharmacodynamics of the compound or compounds used, the nature of the other compounds to be included in the composition, the particular route of administration, the particular characteristics, history and risk factors of the individual, such as, e.g., age, weight, general health and the like, the response of the individual to the treatment, or any combination thereof. An effective dosage amount of active component can thus readily be determined by the person of ordinary skill in the art considering all criteria and utilizing his best judgment on the individual's behalf.

Additionally, where repeated administration of a composition comprising a compound or compounds disclosed herein is used, the actual effect amount of a composition comprising a compound or compounds disclosed herein will further depend upon factors, including, without limitation, the frequency of administration, the half-life of the composition comprising a compound or compounds disclosed herein, or any combination thereof. In is known by a person of ordinary skill in the art that an effective amount of a composition comprising a compound or compounds disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a composition comprising a compound or compounds disclosed herein to a mammal, a therapeutically effective amount generally is in the range of about 0.001 mg/kg to about 100.0 mg/kg. In aspects of this embodiment, an effective amount of a composition comprising a compound or compounds disclosed herein can be, e.g., about 0.01 mg/kg to about 0.1 mg/kg, about 0.03 mg/kg to about 3.0 mg/kg, about 0.1 mg/kg to about 3.0 mg/kg, or about 0.3 mg/kg to about 3.0 mg/kg. In yet other aspects of this embodiment, a therapeutically effective amount of a composition comprising a compound or compounds disclosed herein can be, e.g., at least 0.001 mg/kg, at least 0.01 mg/kg, at least 0.1 mg/kg, at least 1.0 mg/kg, at least 10 mg/kg, or at least 100 mg/kg. In yet other aspects of this embodiment, a therapeutically effective amount of a composition comprising a compound or compounds disclosed herein can be, e.g., at most 0.001 mg/kg, at most 0.01 mg/kg, at most 0.1 mg/kg, at most 1.0 mg/kg, at most 10 mg/kg, or at most 100 mg/kg.

Dosing can be single dosage or cumulative (serial dosing), and can be readily determined by one skilled in the art. For instance, treatment of a cancer may comprise a one-time administration of an effective dose of a composition comprising a compound or compounds disclosed herein. As a non-limiting example, an effective dose of a composition comprising a compound or compounds disclosed herein can be administered once to a mammal, e.g., as a single injection or deposition at or near the site exhibiting a symptom of a cancer or a single oral administration of the drug. Alternatively, treatment of a cancer may comprise multiple administrations of an effective dose of a composition comprising a compound or compounds disclosed herein carried out over a range of time periods, such as, e.g., daily, once every few days, weekly, monthly or yearly. As a non-limiting example, a composition comprising a compound or compounds disclosed herein can be administered once or twice weekly to a mammal. The timing of administration can vary from mammal to mammal, depending upon such factors as the severity of a mammal's symptoms. For example, an effective dose of a composition comprising a compound or compounds disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a composition comprising a compound or compounds disclosed herein that is administered can be adjusted accordingly.

The combined administration, whether concurrently or sequentially, of a thioxanthone-based autophagy inhibitor and a cancer therapeutic autophagy inducing compound provides a synergistic therapeutic effect that is beneficial to the treatment of a cancer as disclosed herein. A synergistic therapeutic effect is one where a symptom associated with cancer is reduced to a greater degree when the compounds or compositions disclosed herein are administered in combination as oppose to when the same compounds are administered individually. In aspects of this embodiment, administration of a compound or composition disclosed herein in combination reduces a symptom associated with a cancer by, e.g., at least 10% more, at least 20% more, at least 30% more, at least 40% more, at least 50% more, at least 60% more, at least 70% more, at least 80% more, at least 90% more or at least 100% more relative to administration of either the same thioxanthone-based autophagy inhibitor or the same cancer therapeutic autophagy inducing compound alone.

A composition comprising a compound or compounds disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Aspects of the present specification disclose, in part, a radiotherapy. In one embodiment, a method of treating cancer by administering a TAPI and CTAPIC disclosed herein may further comprise administering a radiotherapy. A radiotherapy may be administered before, after or during the administration of compounds and compositions disclosed herein. In another embodiment, a method of treating cancer comprises administering a TAPI and a radiotherapy, but not a CTAPIC.

Radiation may be administered in a variety of fashions. For example, radiation may be electromagnetic or particulate in nature. Electromagnetic radiation useful in the practice of this invention includes, but is not limited to, x-rays and gamma rays. In a preferable embodiment, supervoltage x-rays (x-rays>=4 MeV) may be used in the practice of this invention. Particulate radiation useful in the practice of this invention includes, but is not limited to, electron beams, protons beams, neutron beams, alpha particles, and negative pi mesons. The radiation may be delivered using conventional radiological treatment apparatus and methods, and by intraoperative and stereotactic methods. Additional discussion regarding radiation treatments suitable for use in the practice of this invention may be found throughout Steven A. Leibel et al., Textbook of Radiation Oncology (1998) (publ. W. B. Saunders Company), and particularly in Chapters 13 and 14. Radiation may also be delivered by other methods such as targeted delivery, for example by radioactive "seeds," or by systemic delivery of targeted radioactive conjugates. J. Padawer et al., Combined Treatment with Radioestradiol Lucanthone in Mouse C3HBA Mammary Adenocarcinoma and with Estradiol Lucanthone in an Estrogen Bioassay, Int. J. Radiat. Oncol. Biol. Phys. 7:347-357 (1981). Other radiation delivery methods may be used in the practice of this invention.

The amount of radiation delivered to the desired treatment volume may be variable. In a preferable embodiment, radiation may be administered in amount effective to cause the arrest or regression of the cancer of a central nervous system in a host, when the radiation is administered with a compound or compounds, or compositions disclosed herein. In another embodiment, radiation is administered in at least about 1 Gray (Gy) fractions at least once every other day to a treatment volume, and more preferably radiation is administered in at least about 2 Gray (Gy) fractions at least once per day to a treatment volume, even more preferably radiation is administered in at least about 2 Gray (Gy) fractions at least once per day to a treatment volume for five consecutive days per week. In another embodiment, radiation is administered in 3 Gy fractions every other day, three times per week to a treatment volume. In another embodiment, the first 23 fractions are administered to an initial treatment volume, while another 7 treatment fractions are delivered to a boost treatment volume. In yet another embodiment, a total of at least about 20 Gy, still more preferably at least about 30 Gy, most preferably at least about 60 Gy of radiation is administered to a host in need thereof. In another more preferable embodiment, radiation is administered to the whole brain, rather than to a treatment volume. When irradiating the whole brain, a maximum dosage of 30 Gy is recommended. In a most preferable embodiment, radiation is administered to the whole brain of a host, wherein the host is being treated for metastatic cancer.

In a preferable embodiment, the treatment volume comprises a contrast-enhancing lesion on a CT or MRI scan, more preferably a contrast-enhancing lesion and surrounding edema, still more preferably a contrast-enhancing lesion and surrounding edema on a CT or MRI scan plus at least about a 1 cm margin.

Treatment plans may include, but are not limited to, opposed lateral fields, a wedge pair of fields, rotation or multiple field techniques. CT-guided treatment planning is suggested to improve accuracy in the selection of field arrangements. Isodose distributions for the initial treatment volume and the cone-down treatment volume are suggested for all patients, including those with parallel opposed fields. Composite plans showing dose distribution to the initial treatment volume and the boost treatment volume are desirable. The minimum and maximum dose to the treatment volume are preferably kept to within about 10% of the dose at the center of the treatment volume.

Aspects of the present disclosure can also be described as follows:

1. A pharmaceutical composition comprising a therapeutically effective amount of a thioxanthone-based autophagy inhibitor.
2. A pharmaceutical composition comprising a therapeutically effective amount of cancer therapeutic autophagy inducing compound.
3. A pharmaceutical composition comprising:
    a) a therapeutically effective amount of a thioxanthone-based autophagy inhibitor; and
    b) a therapeutically effective amount of a cancer therapeutic autophagy inducing compound.
4. The composition of embodiments 1-3, wherein the composition further comprises a pharmaceutically acceptable carrier.
5. The composition of embodiments 1, 3, or 4, wherein the thioxanthone-based autophagy inhibitor is 1-((2-(Diethylamino)ethyl)amino)-4-methylthioxanthen-9-one, 1-(2-diethylaminoethylamino)-4-(hydroxymethyl)-9-thioxanthenone, N-[[1-[[2-(diethylamino)ethyl]amino]-9-oxo-9H-thiaxanthen-4-yl]methyl]methanesulfonamide, indazole analogues thereof, or salts thereof.
6. The composition of embodiments 2-4, wherein the cancer therapeutic autophagy inducing compound is an arsenic trioxide, an etoposide, a rapamycin, a histone deacetylase inhibitor, a tyrosine kinase inhibitors, a tamoxifen, a temozolomide, an imatinib, or a bortezomib.
7. The composition of embodiment 6, wherein the histone deacetylase inhibitor is a hydroxamate-type histone deacetylase inhibitor or a benzamide-type histone deacetylase inhibitor.
8. The composition of embodiment 6, wherein the histone deacetylase inhibitor is (2E,4E,6R)-7-(4-dimethylaminophenyl)-N-hydroxy-4,6-dimethyl-7-oxohepta-2,4-dienamide, N-hydroxy-N'-phenyloctanediamide, 4-Dimethylamino-N-(6-hydroxycarbamoylhexyl)-benzamide, N-hydroxy-3-[(E)-3-(hydroxyamino)-3-oxoprop-1-enyl]benzamide, (2E)-3-[3-(anilinosulfonyl)phenyl]-N-hydroxyacrylamide, ((E)-N-hydroxy-3-[4-[[2-hydroxyethyl-[2-(1H-indol-3-yl)ethyl]amino]methyl]phenyl]prop-2-enamide, (E)-N-hydroxy-3-[4-[[2-(2-methyl-1H-indol-3-yl)ethylamino]methyl]phenyl]prop-2-enamide, N-(2-aminophenyl)-N'-phenyl-octanediamide, 4-(2-aminophenylcarbamoyl)benzylcarbamate, 4-acetamido-N-(2-aminophenyl)benzamide, N-(2-aminophenyl)-4-[[(4-pyridin-3-ylpyrimidin-2-yl)amino]methyl]benzamide, 3-(dimethylaminomethyl)-N-[2-[4-(hydroxycarbamoyl)phenoxy]ethyl]-1-benzofuran-2-carboxamide, or {6-[(diethylamino)methyl]-2-naphthyl}methyl {4-[(hydroxyamino)carbonyl]phenyl}carbamate.
9. A use of a composition according to embodiments 1-8 for the manufacture of a medicament to treat cancer.

10. A method of treating cancer, the method comprising
   a) administering an effective amount of a thioxanthone-based autophagy inhibitor of embodiments 1 or 3-6 to a mammal in need thereof; and
   b) administering an effective amount of a cancer therapeutic autophagy inducing compound of embodiments 2-6 to a mammal in need thereof;
   wherein the administration of both the thioxanthone-based autophagy inhibitor and the cancer therapeutic autophagy inducing compound reduces a symptom associated with cancer, thereby treating the cancer.
11. A use of a composition according to embodiments 1-8 for the treatment of cancer, wherein the administration of both the thioxanthone-based autophagy inhibitor and the cancer therapeutic autophagy inducing compound reduces a symptom associated with cancer, thereby treating the cancer.
12. The method of embodiment 10 or the use of embodiment 11, wherein the thioxanthone-based autophagy inhibitor and cancer therapeutic autophagy inducing compound are administered concurrently.
13. The method of embodiment 10 or the use of embodiment 11, wherein the thioxanthone-based autophagy inhibitor and the cancer therapeutic autophagy inducing compound are administered sequentially.
14. The method or use of embodiment 13, wherein the thioxanthone-based autophagy inhibitor and the cancer therapeutic autophagy inducing compound are administered within about three hours of each other.
15. The method or use of embodiment 13, wherein the thioxanthone-based autophagy inhibitor and the cancer therapeutic autophagy inducing compound are administered within about two hours of each other.
16. The method or use of embodiment 13, wherein the thioxanthone-based autophagy inhibitor and the cancer therapeutic autophagy inducing compound are administered within about one hour of each other.
17. The method of embodiment 10 or the use of embodiment 11, wherein said therapeutically effective amount of the thioxanthone-based autophagy inhibitor and the therapeutically effective amount of the cancer therapeutic autophagy inducing compound are administered in a single daily dose or divided into more than one daily dose.
18. The method or use of embodiment 17, wherein said more than one daily dose is two daily doses.
19. The method of embodiment 10 or the use of embodiment 11, wherein the thioxanthone-based autophagy inhibitor and the cancer therapeutic autophagy inducing compound are administered orally.
20. The method of embodiment 10 or the use of embodiment 11, wherein the thioxanthone-based autophagy inhibitor and the cancer therapeutic autophagy inducing compound are administered parenterally.
21. The method of embodiment 10 or the use of embodiment 11, wherein the thioxanthone-based autophagy inhibitor and the cancer therapeutic autophagy inducing compound are administered in the form of a capsule or tablet.
22. The method of embodiment 10 or the use of embodiment 11, wherein thioxanthone-based autophagy inhibitor and the cancer therapeutic autophagy inducing compound are administered for one or more cycles.
23. The method of embodiment 10 or the use of embodiment 11, wherein said one cycle comprises 7 times every 4 days.
24. The method of embodiments 10, or 12-23 or the use of embodiments 11-23, wherein the cancer is a lung cancer, a brain cancer, a central nervous system cancer, a breast cancer, a colon cancer, a leukemia, a myeloma, a prostate, or an ovarian cancer.
25. The method or use of embodiment 24, wherein the lung cancer is non-small lung carcinoma.
26. The method or use of embodiments 10-25, wherein the method or use further comprises administering radiation therapy, hormonal therapy or immunotherapy.
27. A pharmaceutical kit comprising:
   a) a pharmaceutical composition comprising a therapeutically effective amount of a thioxanthone-based autophagy inhibitor and a pharmaceutically acceptable carrier, and
   b) a pharmaceutical composition comprising a therapeutically effective amount of a cancer therapeutic autophagy inducing compound and a pharmaceutically acceptable carrier.
28. A method of treating cancer, the method comprising
   a) administering an effective amount of a thioxanthone-based autophagy inhibitor of embodiments 1, 4, or 5 to a mammal in need thereof; and
   b) administering an effective amount of an ionizing radiation to a mammal in need thereof;
   wherein the administration of both the thioxanthone-based autophagy inhibitor and the ionizing radiation reduces a symptom associated with cancer, thereby treating the cancer.
29. A method of treating cancer, the method comprising
   a) administering an effective amount of a thioxanthone-based autophagy inhibitor of embodiments 1 or 3-6 to a mammal in need thereof;
   b) administering an effective amount of a cancer therapeutic autophagy inducing compound of embodiments 1, 4, or 6-8 to a mammal in need thereof; and
   c) administering an effective amount of an ionizing radiation to a mammal in need thereof;
   wherein the administration of the thioxanthone-based autophagy inhibitor, the cancer therapeutic autophagy inducing compound, and the ionizing radiation reduces a symptom associated with cancer, thereby treating the cancer.
31. A use of a composition according to embodiments 1, 4, or 5 for the treatment of cancer to a mammal in need thereof, wherein the administration of the thioxanthone-based autophagy inhibitor, in conjunction with administering an effective amount of an ionizing radiation, reduces a symptom associated with cancer, thereby treating the cancer.
32. A use of a composition according to embodiments 1-8 for the treatment of cancer to a mammal in need thereof, wherein the administration of the thioxanthone-based autophagy inhibitor, the cancer therapeutic autophagy inducing compound, or both, in conjunction with administering an effective amount of an ionizing radiation, reduces a symptom associated with cancer, thereby treating the cancer.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, pharmaceutical kits, or methods of treating cancer.

Example 1

Lucanthone Inhibits Autophagic Degradation

Lucanthone induces lysosomal membrane permeabilization (LMP). Autophagy promotes cell survival and leads to drug resistance by enabling cancer cells to recycle cellular components to generate ATP. In accordance with this, inhibition of autophagy genetically or using compounds such as 3-MA enhances the activity of many anticancer agents. Lucanthone is an anti-schistome agent that based on its chemical structure, could disrupt lysosomal function and inhibit the last step in autophagic degradation. To test this hypothesis, breast cancer cells were treated with Lucanthone or chloroquine and assayed for the accumulation of LC3-II, an increase in vacuolization, and the appearance of lysosomal membrane permeabilization.

Accumulation of LC3-II was visualized by immunocytochemistry. Cells from a MDA-MB-231 breast cancer cell line were plated on chamber slides and allowed to attach overnight. Cells were then treated for 48 hours with 10 µM Lucanthone or 50 µM Chloroquine. Following drug treatment, cells were fixed with 4% paraformaldehyde, permeabilized using 0.2% TRITON-X-100, and incubated overnight with indicated primary antibodies. Alexa Fluor 488 conjugated fluorescent secondary antibodies were used to visualize protein localization. Images were captured using an Olympus fluorescent microscope (Center Valley, Pa.) with a DP71 camera and a 60× objective. Image-Pro Plus software Version 6.2.1 (MediaCybernetics, Bethesda, Md.) was used for image acquisition.

Increased vacuolization was visualized by Giemsa staining and transition electron microscopy. Cells from a MDA-MB-231 breast cancer cell line were plated in chamber slides and treated with 10 µM Lucanthone or 50 µM Chloroquine for 48 hours. After drug treatment, cells were washed with PBS and fixed in methanol for 5 minutes. Cells were then incubated for 1 hour in Giemsa stain diluted 1:20 with deionized water. Cells were rinsed with water and imaged using an Olympus fluorescent microscope. Image-Pro Plus software Version 6.2.1 was used for image acquisition. Transmission electron microscopy of cells was performed using routine procedures. Sections were cut in an LKB Ultracut microtome (Leica, Deerfield, Ill.), stained with uranyl acetate and lead citrate, and examined in a JEM 1230 transmission electron microscope (JEOL, USA, Inc., Peabody, Mass.). Images were captured using the AMT Imaging System (Advanced Microscopy Techniques Corp, Danvers, Mass.).

The appearance of LMP was monitored by loss of acridine orange fluorescence. Acidic lysosomes were visualized by acridine orange staining. After treatment with 10 µM Lucanthone or 50 µM Chloroquine for 48 hours, cells from a MDA-MB-231 breast cancer cell line were stained with 1 µM acridine orange for 15 minutes at 37° C. Cells were washed with PBS and images were captured using an Olympus fluorescent microscope. Based on the acidity, lysosomes appeared as orange fluorescent cytoplasmic vesicles. Quantification of 5 random fields of acridine orange intensity was measured by immunofluorescence and image acquisition were performed using Image-Pro Plus software Version 6.2.1.

Lucanthone induced lipid modification of LC3-1 into LC3-II, which is characterized by the punctuate localization of LC3 to autophagosomes (FIG. IB). Lucanthone also induced cytoplasmic vacuolization, which is characteristic of lysosomal membrane permeabilization and autophagy (FIG. IB). Furthermore, Lucanthone decreased the red staining intensity of lysosomes with acridine orange indicating a loss of lysosomal acidity following treatment with Chloroquine and Lucanthone (FIGS. IB and IC).

Inhibition of autophagy results in an accumulation of proteins. Lucanthone or Chloroquine induced an accumulation of electron dense particles when visualized by transmission electron microscopy, suggesting protein aggregation (FIG. IB). To confirm this finding, breast cancer cells were treated with Lucanthone or Chloroquine and assayed for the accumulation of the polyubiquitin-binding protein p62 or sequestosome I (SQSTMI). This protein is degraded by autophagy, localized to cellular inclusion bodies, and has been proposed to play a role in facilitating protein aggregate clearance by autophagy. As such, a disruption of this process would result in the accumulation of SQSTMI/p62.

Levels and aggregation of SQSTMI/p62 were determined by immunoblotting and immunocytochemistry, respectively. For immunoblotting, MDA-MB-231 breast cancer cell line cancer cells were incubated with 10 µM Lucanthone or 50 µM Chloroquine for 48 hours. Cells were harvested and were then lysed using routine procedures. Approximately 50 µg of total cellular protein from each sample were subjected to SDS-PAGE, proteins were transferred to nitrocellulose membranes, and the membranes were blocked with 5% nonfat milk in a Tris-buffered saline solution containing 0.1% TWEEN-20 for 1 hour. The blots were then probed overnight at 4° C. with primary antibodies, washed, and probed with species-specific secondary antibodies coupled to horseradish peroxidase. Immunoreactive material was detected by enhanced chemiluminescence (West Pico, Pierce, Inc., Rockville, Ill.).

Consistent the other markers of autophagy inhibition SQSTMI/p62 levels were strongly increased following treatment with Lucanthone (FIG. ID). Immunocytochemistry revealed that SQSTMI/p62 displayed a diffuse staining pattern under basal conditions, but aggregated in response to Lucanthone. These results indicate that Lucanthone stimulates SQSTM1/p62 accumulation and aggregation, an effect in accord with its reported interaction with ubiquitinated proteins (FIG. ID).

Example 2

Lucanthone is Cytotoxic to Breast Cancer Cells

Lysosomal membrane permeabilization and subsequent inhibition of autophagy had been reported to induce cell death in cancer cells. To investigate the anticancer activity of Lucanthone, cell viability was measured by MTT assay using a panel of seven breast cancer cell lines.

Cells from the breast cancer cell lines MDA-MB-231, HCC1954, BT-474, SKBR-3, MDA-MB-435, HCC1937, and BT-20 were seeded into 96-well microculture plates at 10,000 cells per well and allowed to attach for 24 hours. Cells were then treated with varying concentrations of Lucanthone or Chloroquine for 72 hours. Following drug treatment, 3-(4,5-dimethylthiazol-2-yl)-2,5,diphenyltetrazolium bromide (MTT) was added and cell viability was quantified using a BioTek (Winooski, Vt.) microplate reader. Pro-apoptotic effects following in vitro drug exposure were quantified by propidium iodide (PI) staining and fluorescence-activated cell sorting (FACS) analysis of sub-$G_0$/$G_1$ DNA content. Data is representative of three independent experiments. $IC_{50}$ values were calculated from the results of the MTT assays.

Figure 2A:
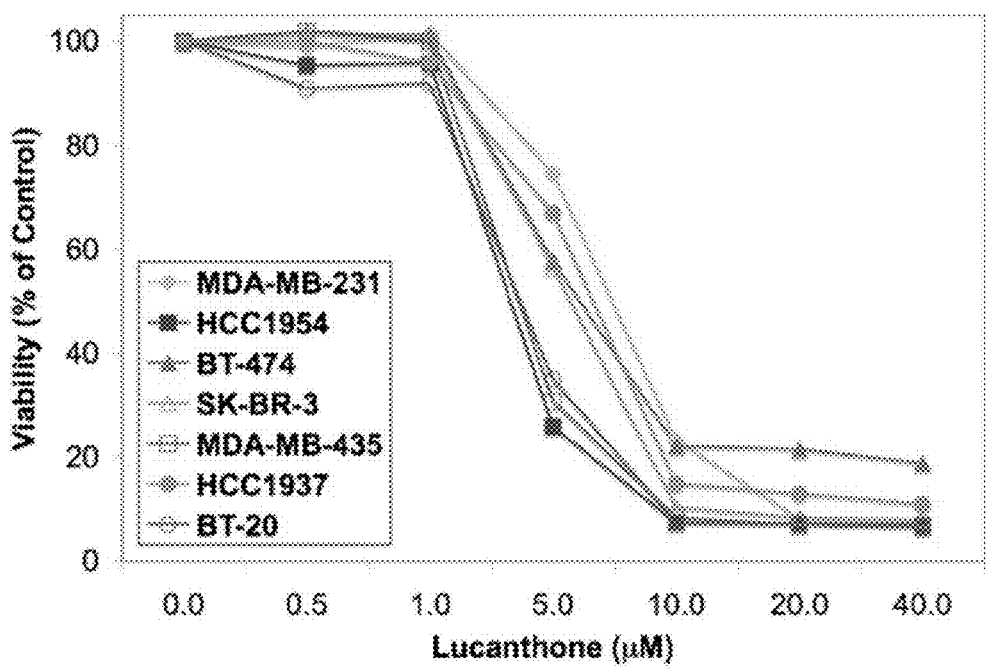
FIG. 2A. Dose response curve of Lucanthone in seven breast cancer cell lines.
Figure 2B:
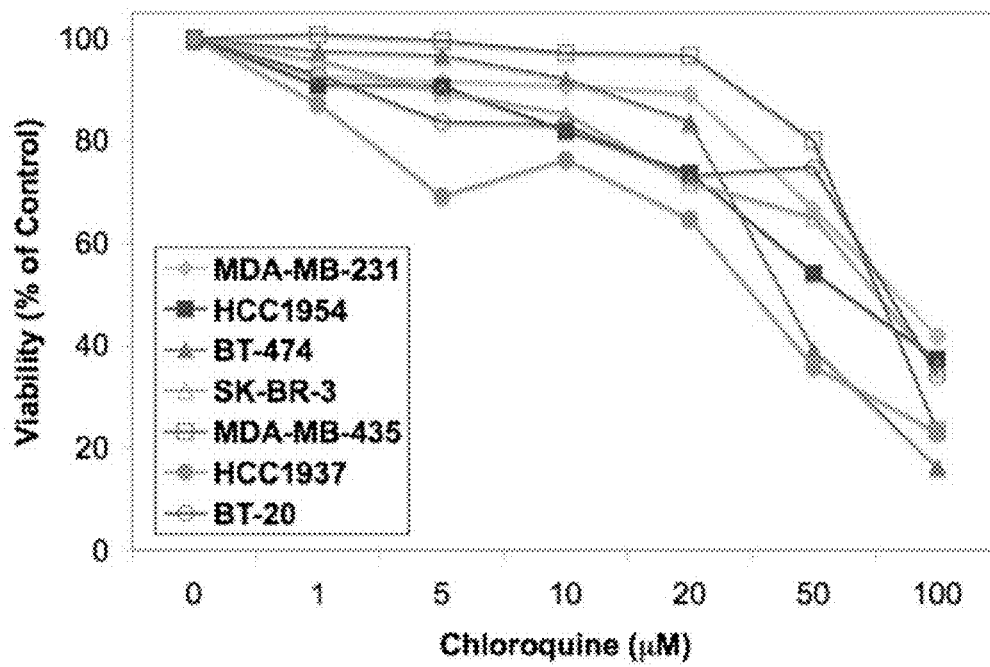
FIG. 2B. Dose response curve of Chloroquine in seven breast cancer cell lines.

Lucanthone reduced cell viability to a similar extent in a panel of seven breast cancer cell lines (FIG. 2). In addition, a direct comparison revealed that Lucanthone was significantly more potent than CQ at reducing breast cancer cell viability with a mean $IC_{50}$ of 7.2 µM versus 66 µM for CQ (FIG. 2).

Example 3

Lucanthone Induces Cathepsin D Expression

Characterization of Lucanthone effects on cancer cells using Affymetrix expression arrays. To further characterize the effects of Lucanthone on breast cancer cells, expression profiling was performed on breast cancer cell lines. Cells from a MDA-MB-231 and a BT-20 breast cancer cell line were treated with 10 µM Lucanthone for 48 hours. Total RNA was isolated using the RNeasy Plus Mini Kit (Qiagen, Germantown, Md.) and treated with TURBO DNA-free™ Kit (Applied Biosystems, Foster City, Calif.). 300 ng of total RNA per sample was amplified and hybridized to GENE-CHIP® Human Gene 1.0 ST arrays (Affymetrix, Inc., Santa Clara, Calif.) according to the manufacturer's instructions. These arrays assay for the expression of about 28,869 well-annotated genes with 764,885 distinct probes. Affymetrix CEL files were imported into PARTEK® Genomics Suite™ 6.4 (Partek Inc., St. Louis, Mo.) using the default Partek normalization parameters and the robust multi-array average (RMA) analysis adjusted for probe sequence and GC content (GC-RMA). Data normalization was performed across all arrays using quantile normalization. Significantly up-regulated genes ($p<0.05$ and >4-fold increase) were identified. Data represents genes upregulated by at least 4-fold following Lucanthone treatment.

Figure 3A:
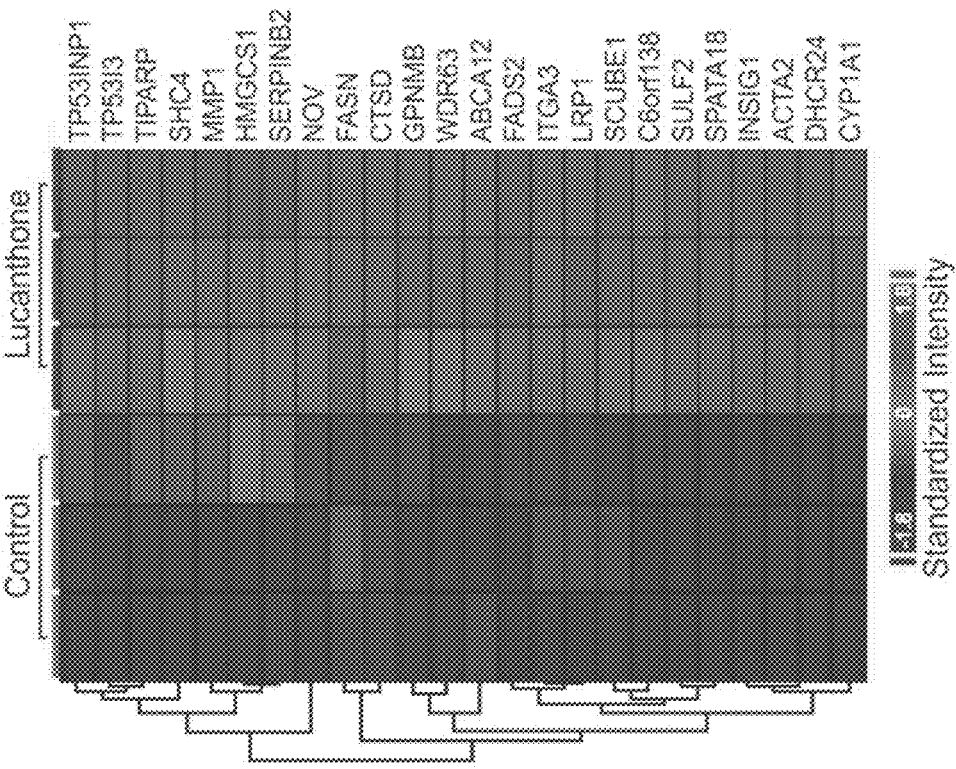
FIG. 3A. Affymetrix expression arrays identify cathepsin D (CTSD) as a strongly upregulated gene in breast cancer cells.
Figure 3A:
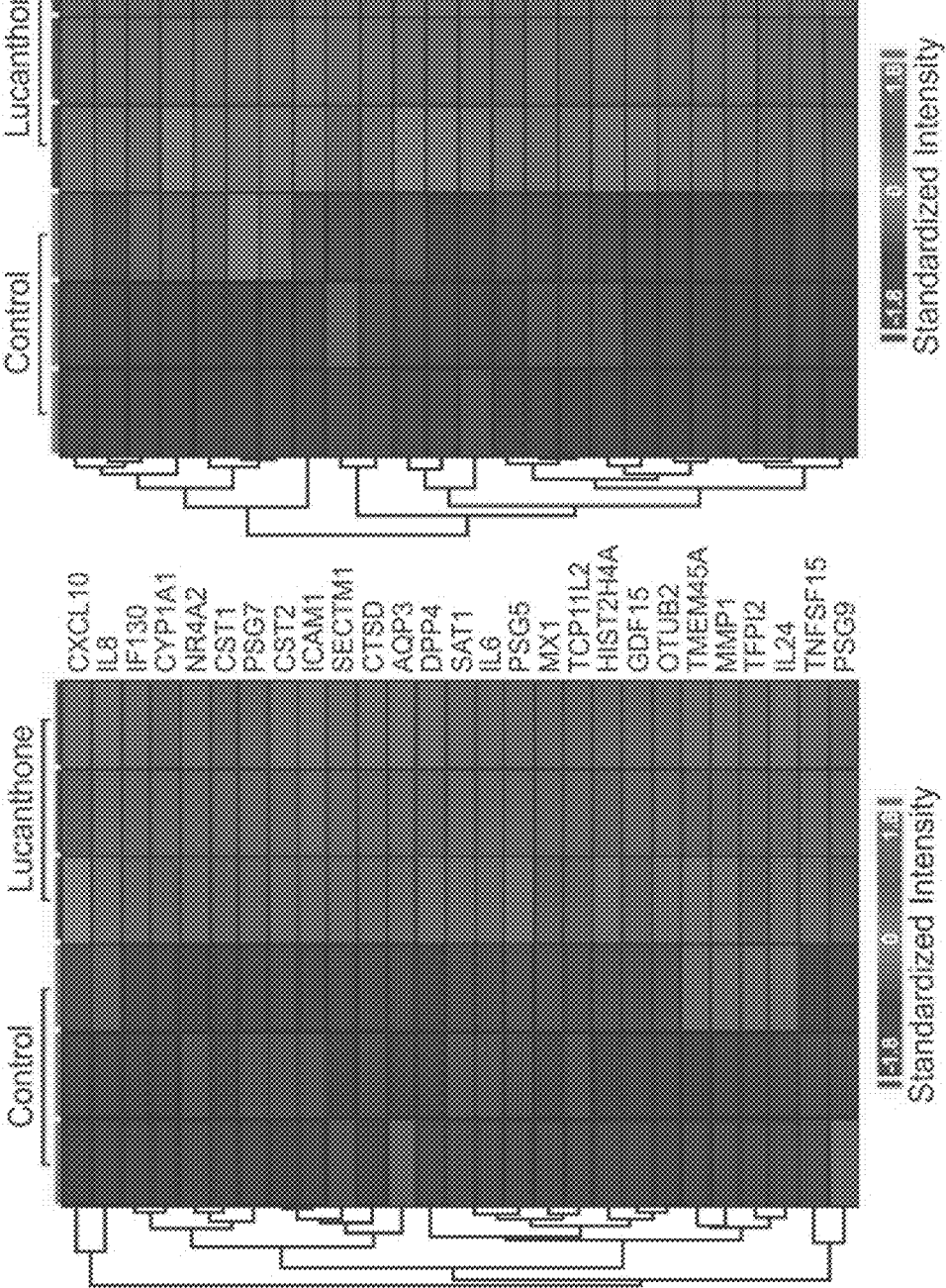

Of the genes induced by Lucanthone, cathepsin D (CTSD), matrix metalloproteinase-I (MMPI), and cytochrome P450, family 1, member AI (CYPIAI) were increased in both cell lines (FIG. 3A).

Quantitative real-time PCR analysis of cathepsin D. The lysosomal protease cathepsin D is a key mediator of apoptosis and its release into the cytosol has been reported to promote cell death. Considering this, we further evaluated the role of cathepsin D during Lucanthone-mediated cell death using quantitative real-time PCR (qRT-PCR). To perform qRT-PCR, cells from a MDA-MB-231 or a BT-20 cell lines were treated with 10 µM Lucanthone for 48 hours and then harvested for analysis. Total RNA was isolated using the RNeasy Plus Mini Kit (Qiagen, Germantown, Md.) and treated with TURBO DNAfree™ Kit (Applied Biosystems, Foster City, Calif.). First-strand cDNA synthesis was performed from 1 µg RNA in a 20 µL reaction mixture using the high-capacity cDNA Reverse Transcription Kit (Applied Biosystems, Foster City, Calif.). Cathepsin D and GAPDH transcripts were amplified using commercially available TaqMan@ Gene expression assays (Applied Biosystems, Foster City, Calif.). Levels of mRNAs were standardized to the expression of GAPDH and relative gene expression was calculated with the $2^{-\Delta Ct}$ method.

Figure 3B:
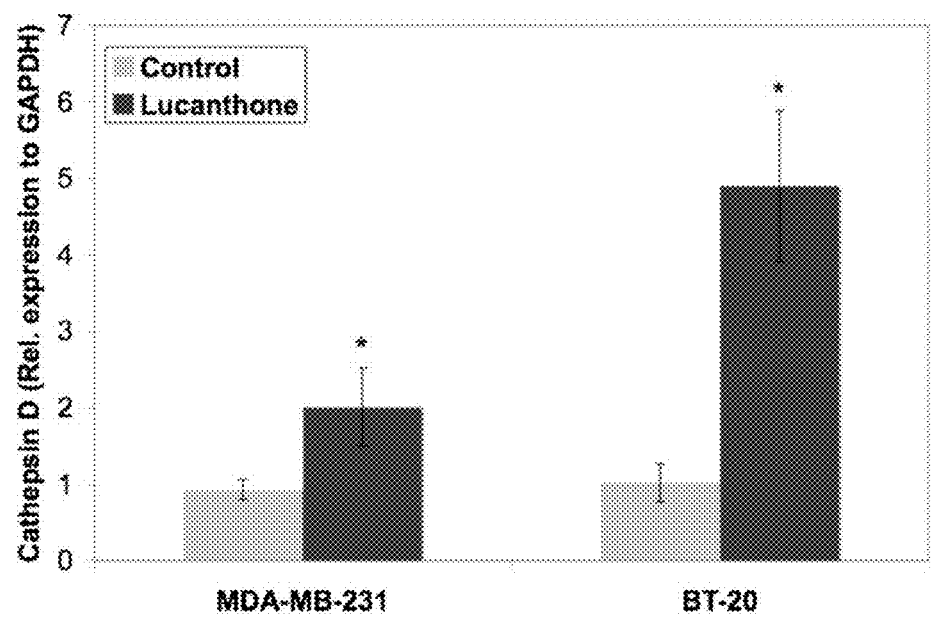
FIG. 3B. Quantitative real-time PCR analysis of cathepsin D expression in breast cancer cells. Mean±standard deviation, n=4. *Indicates a significant difference from the controls. $P<0.05$.
Figure 3C:
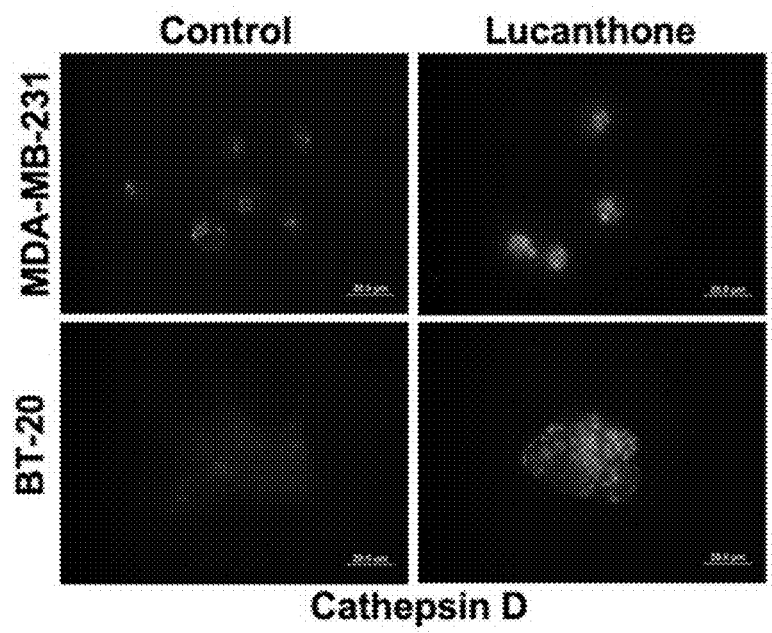
FIG. 3C. Lucanthone increases cathepsin D levels and promotes its aggregation.

Quantitative real-time PCR (qRT-PCR) confirmed that Lucanthone induced a significant increase in cathepsin D levels in both cell lines (FIG. 3B). Furthermore, Lucanthone also dramatically increased cathepsin D protein levels and promoted its cytosolic aggregation as measured by immunocytochemistry (FIG. 3C).

Example 4

Cathepsin D Induction Contributes to Lucanthone-Mediated Apoptosis

Figure 4A:
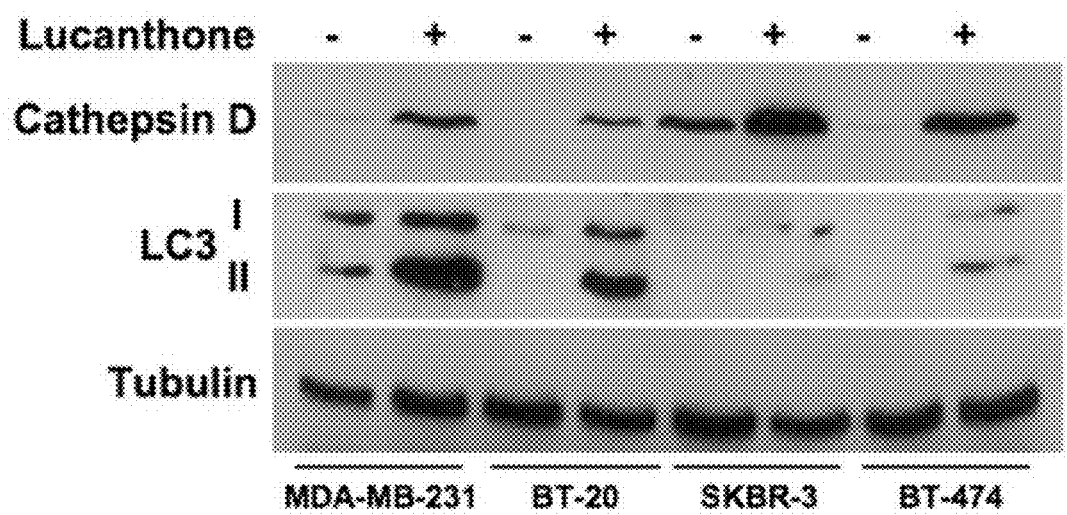
FIG. 4A. Lucanthone induces cathepsin D expression and LC3-II formation.
Figure 4B:
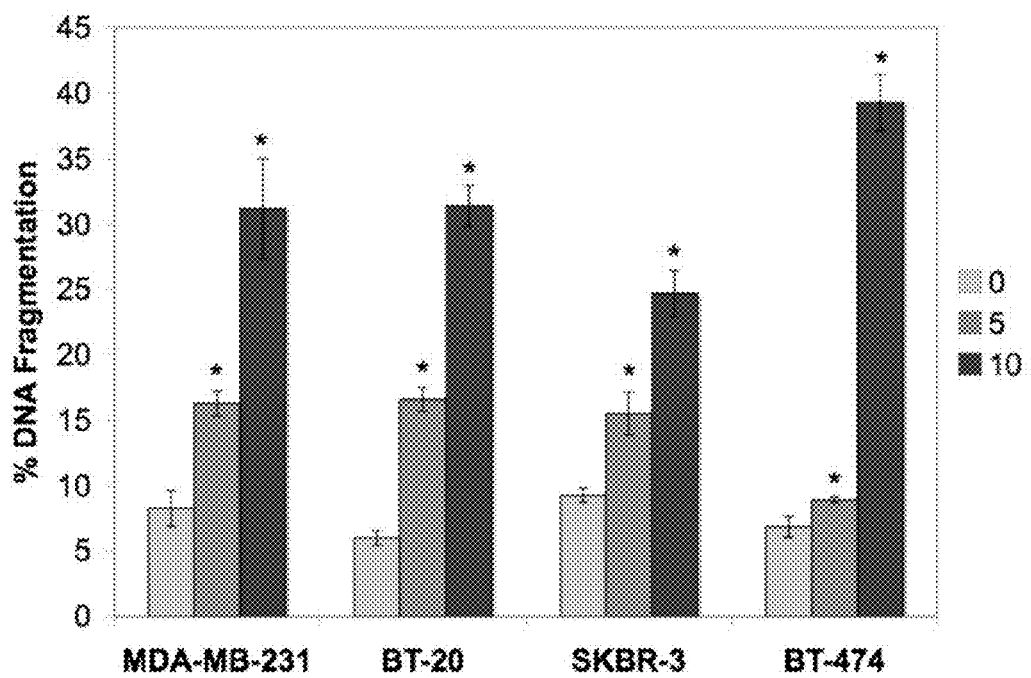
FIG. 4B. Lucanthone induces apoptosis in four different breast cancer cell lines. Mean±standard deviation, n=3. *Indicates a significant difference from controls. $P<0.05$. Figure C. Cathepsin D knockdown diminishes Lucanthone induced apoptosis as shown by immunoblotting. Figure D. Quantification of Lucanthone induced apoptosis reduction by Cathepsin D knockdown. Mean±SD, n=3. *Indicates significant difference from non-target siRNA transfected cells treated with Lucanthone. $P<0.05$.

Cathepsin D expression in breast cancer. As Cathepsin D significantly contributed to Lucanthone-mediated apoptosis, the expression of cathepsin D by immunoblotting and apoptosis by PI-FACS were investigate in four breast cancer cell lines. Cells from the breast cancer cell lines MDA-MB-231, BT-474, SKBR-3, and BT-20 were seeded into 96-well microculture plates at 10,000 cells per well and allowed to attach for 24 hours. Cells were then treated with 10 µM Lucanthone for 72 hours (48 hours for apoptosis assay). For immunoblotting, cells were harvested after treatment and cathepsin D levels were determined as described above. Pro-apoptotic effects following in vitro drug exposure were quantified by propidium iodide (PI) staining and fluorescence-activated cell sorting (FACS) analysis of sub-$G_o/G_1$ DNA content. Data is representative of three independent experiments. As expected, cathepsin D levels were strongly increased following Lucanthone treatment (FIG. 4A) and correlated with apoptosis (FIG. 4B).

Figure 4C:
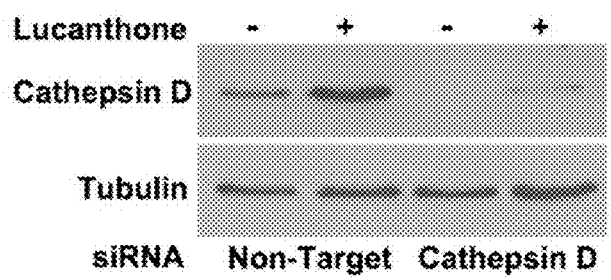
FIG. 4. Induction of cathepsin D contributes to Lucanthone-mediated apoptosis.
Figure 4D:
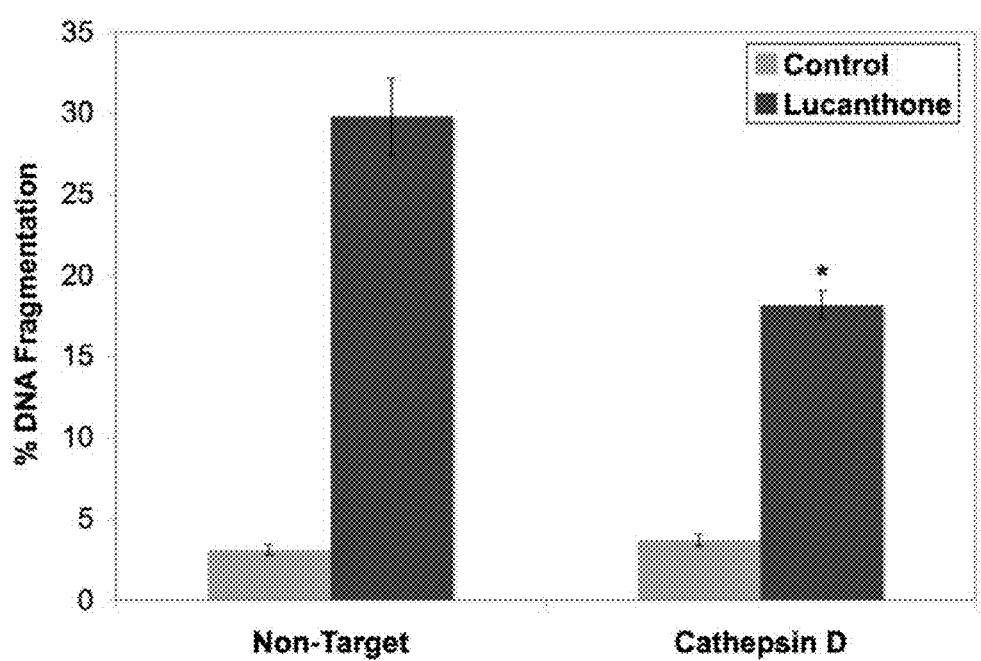

Cathepsin D knockdown diminishes Lucanthone induced apoptosis. To further establish the mechanistic role of cathepsin D in Lucanthone-induced apoptosis, siRNA was used to knockdown its expression (FIG. 4C). Preparation of siRNAs Cathepsin D and non-target SMARTpool siRNA were obtained from Dharmacon (Lafayette, Colo.). Cells from a MDA-MB-231 breast cancer cell line were transfected with 100 nM of either non-target or cathepsin D siRNA using Oligofectamine (Invitrogen, Carlsbad, Calif.) according to the manufacturers protocol. Transfected cells were incubated at 37° C. for 24 hours and then treated with 10 µM Lucanthone for 48 hours. Efficiency of RNAi was measured at 48 hours by immunoblotting using an α-cathepsin D antibody. Apoptosis was determined by PI staining and flow cytometry. The results indicated that cells with reduced cathepsin D levels were significantly less sensitive to Lucanthone-mediated apoptosis (FIG. 4D).

Example 5 p53 Does not Diminish Cathepsin D Accumulation or Activity of Lucanthone

Figure 5A:
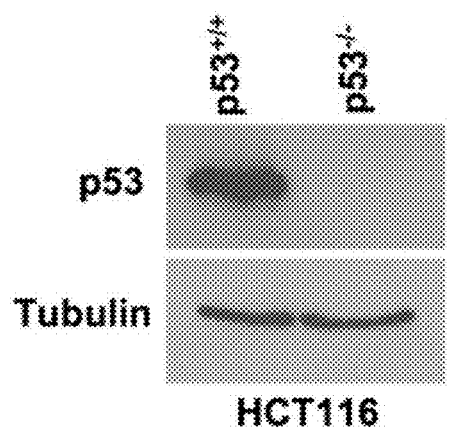
FIG. 5A. HCT116 p53+/+ and p53−/− cells were used to evaluate whether p53 was required for Lucanthone-mediated apoptosis.
Figure 5B:
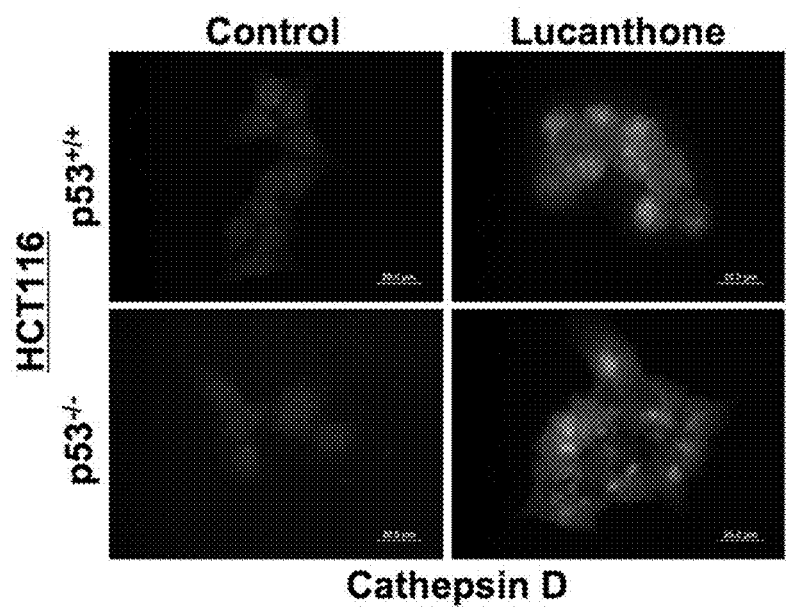
FIG. 5B. Lucanthone increases cathepsin D levels in HCT116 cells independent of p53 status.
Figure 5C:
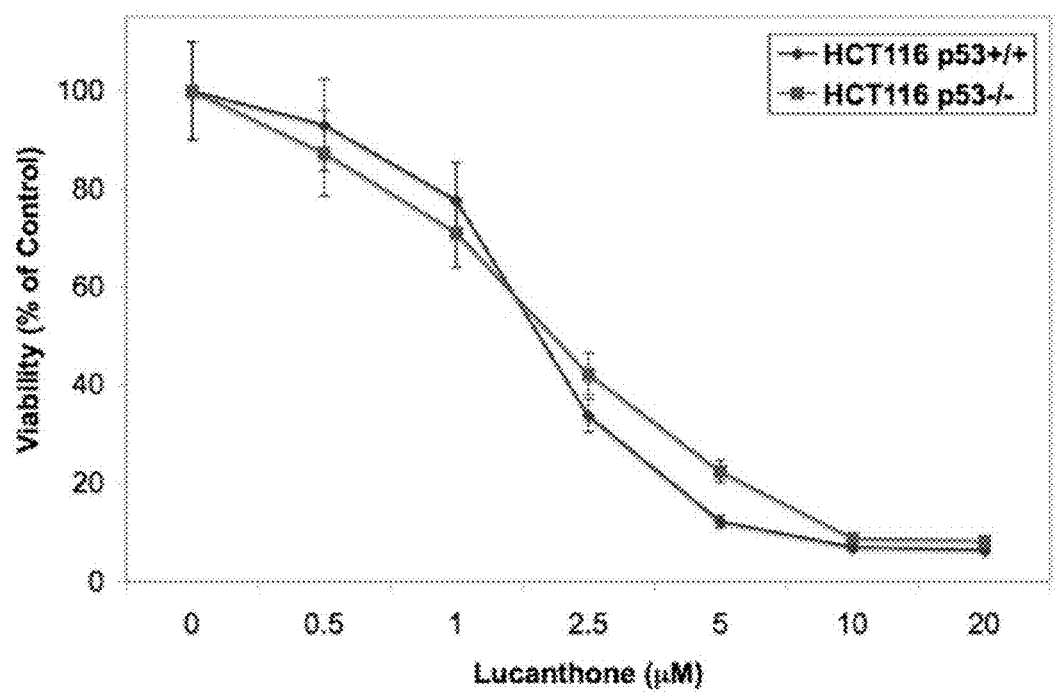
FIG. 5C. HCT116 p53+/+ and p53−/− cells are equally sensitive to Lucanthone. Mean±standard deviation, n=3.

Loss of function of p53 is a frequent event in human cancer that is associated with tumorigenesis and drug resistance. Therefore, agents that possess efficacy independent of p53 status are highly desirable. To investigated the role of p53 in Lucanthone-mediated cell death, isogenic p53+1$^+$ and p53−1$^-$ HCT116 colorectal cancer cell lines (FIG. 5A). Importantly, Lucanthone induced cathepsin D accumulation equally regardless of p53 status (FIG. 5B). Consistent with equipotent induction of cathepsin D, Lucanthone reduced viability to a similar extent in both HCT116 p53+1$^+$ and p53−1$^-$-cell lines (FIG. 5C). As such, loss of p53 does not diminish cathepsin D accumulation or activity of Lucanthone.

Example 6

Lucanthone Enhances the Activity of Vorinostat

Since Lucanthone inhibits autophagy, it may also be able to enhance the activity of chemotherapeutic agents that induce this pathway. The thioxanthone-based autophagy inhibitor Vorinostat induces both apoptosis and autophagy and inhibition of autophagy strongly potentiates its pro-apoptotic activity. To determine whether a combined Lucanthone and Vorinostat would be effective, the expression of cathepsin D by immunoblotting, cell viability by MTT assay, and apoptosis by PI-FACS were investigate in four breast cancer cell lines.

Cells from the breast cancer cell lines MDA-MB-231, BT-474, SKBR-3, and BT-20 were seeded into 96-well microculture plates at 10,000 cells per well and allowed to attach for 24 hours. For immunoblotting, cells were then treated with 10 µM Lucanthone, 2.5 µM Vorinostat, or the combination for 72 hours, harvested, and cathepsin D levels were determined as described above. For the MTT cell viability assay, the cells were then treated with 10 µM Lucanthone, 2.5 µM Vorinostat, or the combination for 72 hours. After treatment, 3-(4,5-dimethylthiazol-2-yl)-2,5,diphenyltetrazolium bromide (MTT) was added after treatment and cell viability was quantified using a BioTek (Winooski, Vt.) microplate reader. For apoptosis assay, the cells were then treated with 10 µM Lucanthone, 2.5 µM Vorinostat, or the combination for 48 hours. Pro-apoptotic effects following in vitro drug exposure were quantified by propidium iodide (PI) staining and fluorescence-activated cell sorting (FACS) analysis of sub-$G_0/G_1$ DNA content. Data is representative of three independent experiments.

Figure 6A:
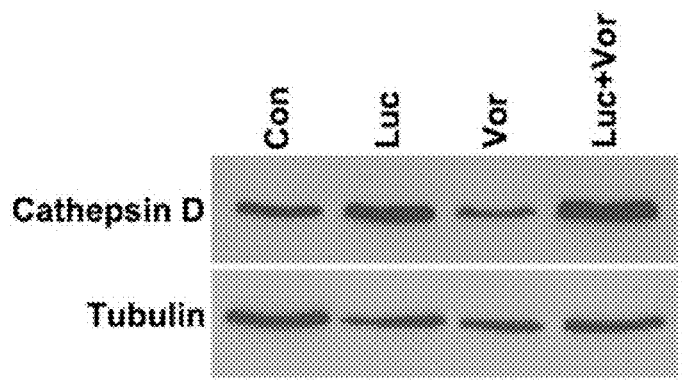
FIG. 6A. The combination of Lucanthone and Vorinostat increases cathepsin D levels.
Figure 6B:
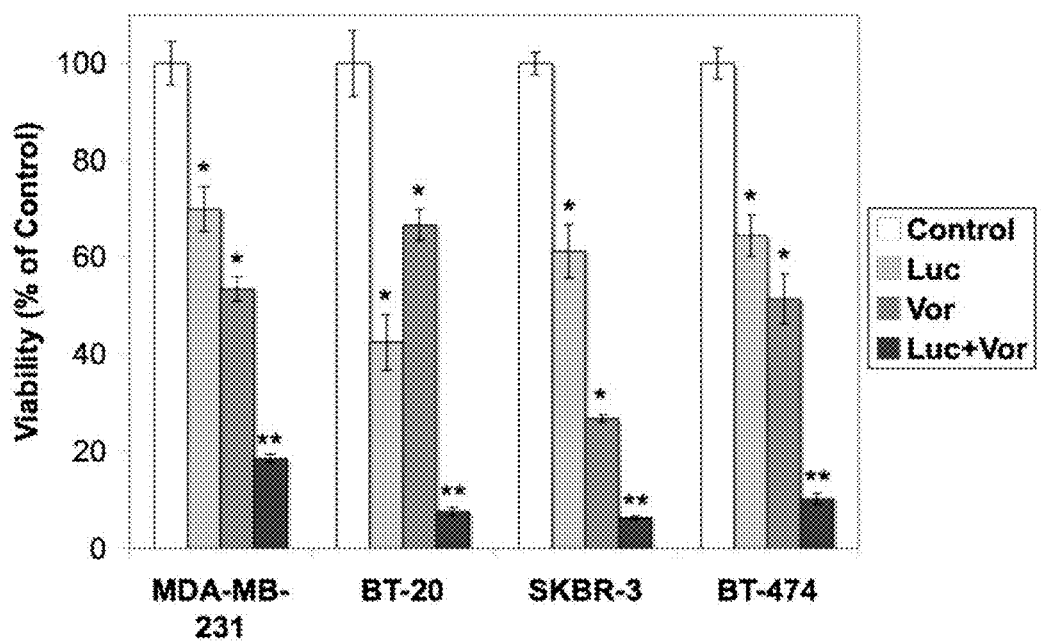
FIG. 6B. Quantification of the effects of Lucanthone and Vorinostat on breast cancer cell viability. Mean±standard deviation, n=3. *Indicates a significant difference compared to controls. **Indicates a significant difference compared to single agent groups. $P<0.05$.
Figure 6C:
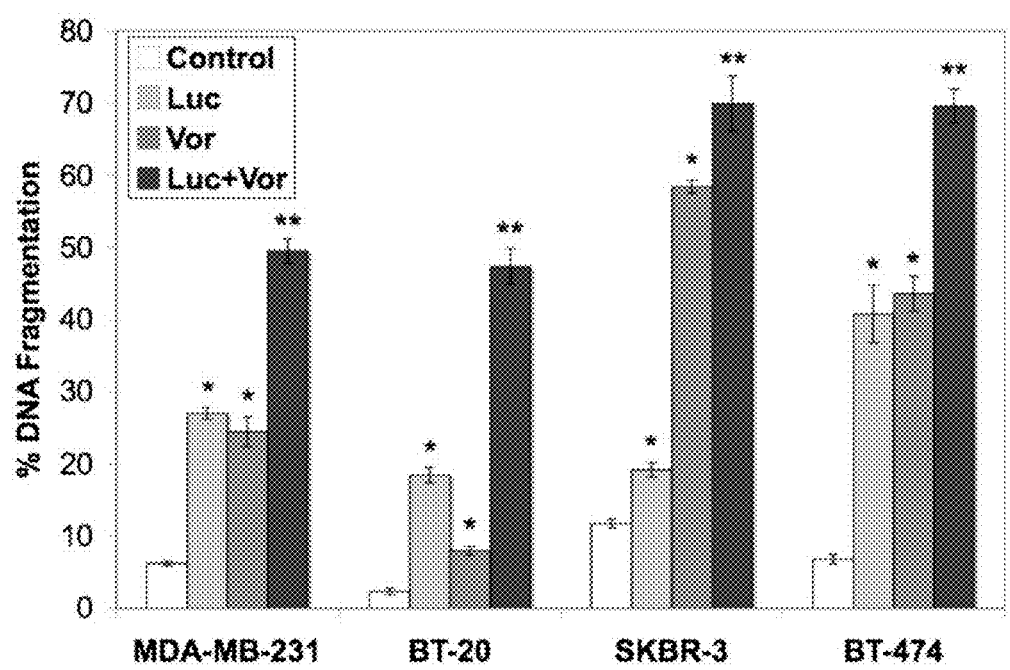
FIG. 6C. Lucanthone enhances Vorinostat-mediated apoptosis. Mean±standard deviation, n=3. *Indicates a significant difference compared to controls. **Indicates a significant difference compared to single agent groups. $P<0.05$.

The combination of Lucanthone and Vorinostat led to increased induction of cathepsin D in MDA-MB-231 cells over what was achieved by either single agent treatment (FIG. 6A), which was associated with decreased cell viability (FIG. 6B) and increased apoptosis (FIG. 6C). These data provide evidence that inhibition of autophagy with Lucanthone can successfully augment the anticancer activity of Vorinostat.

Example 7

Lucanthone Enhances the Activity of Belinostat

To further explore and expand the findings that Lucanthone can successfully augment the anticancer activity of HDAC inhibitors, we investigated the efficacy of lucanthone in combination with another HDAC inhibitor, Belinostat by assessing cell viability by MTT assay, and apoptosis by PI-FACS were investigate in four breast cancer cell lines.

Cells from the breast cancer cell lines MDA-MB-231 and BT-20 were seeded into 96-well microculture plates at 10,000 cells per well and allowed to attach for 24 hours. For the MTT cell viability assay, the cells were then treated with 5 µM Lucanthone, 1 µM Belinostat, or the combination for 72 hours. After treatment, 3-(4,5-dimethylthiazol-2-yl)-2,5, diphenyltetrazolium bromide (MTT) was added after treatment and cell viability was quantified using a BioTek (Winooski, Vt.) microplate reader. For the apoptosis assay, the cells were then treated with 10 µM Lucanthone, 1 µM Belinostat, or the combination for 48 hours. Pro-apoptotic effects following in vitro drug exposure were quantified by propidium iodide (PI) staining and fluorescence-activated cell sorting (FACS) analysis of sub-$G_0/G_1$ DNA content. Data is representative of three independent experiments.

Figure 7A:
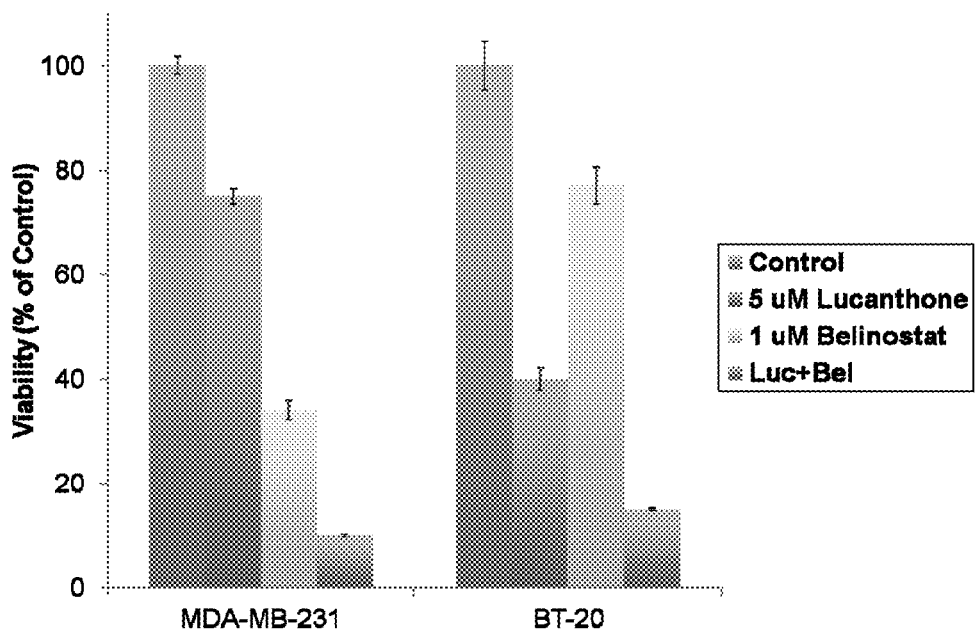
FIG. 7A. Quantification of the effects of Lucanthone and Belinostat on breast cancer cell viability. Mean±standard deviation, n=3. *Indicates a significant difference compared to controls. **Indicates a significant difference compared to single agent groups. $P<0.05$.
Figure 7B:
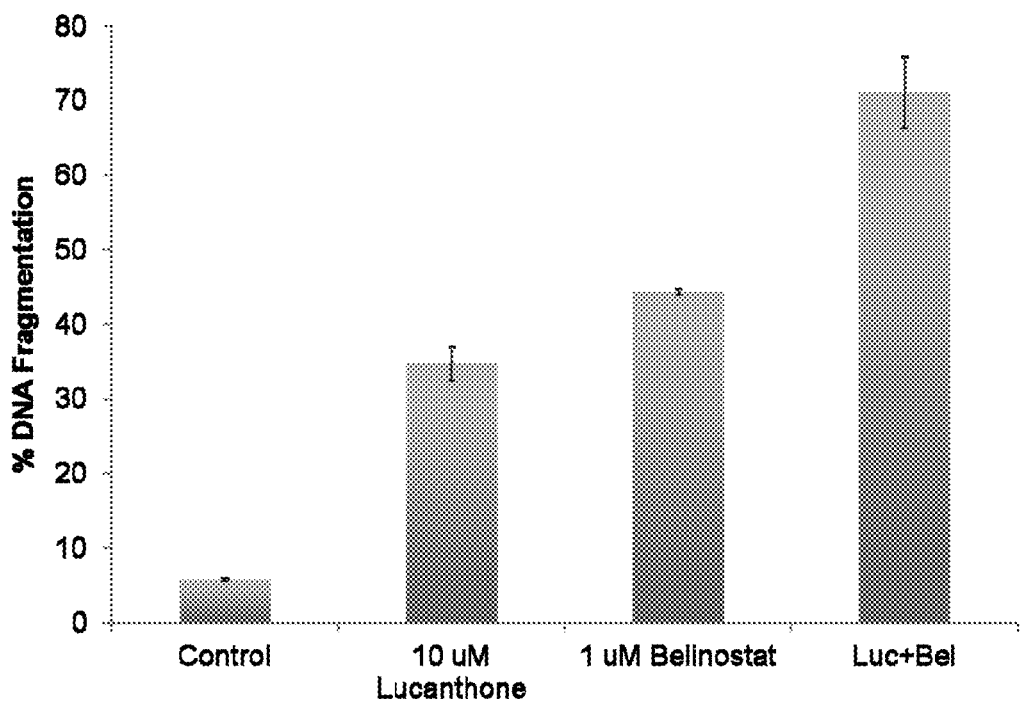
FIG. 7B. Lucanthone enhances Belinostat-mediated apoptosis. Mean±standard deviation, n=3. *Indicates a significant difference compared to controls. **Indicates a significant difference compared to single agent groups. $P<0.05$.
Figure 7C:
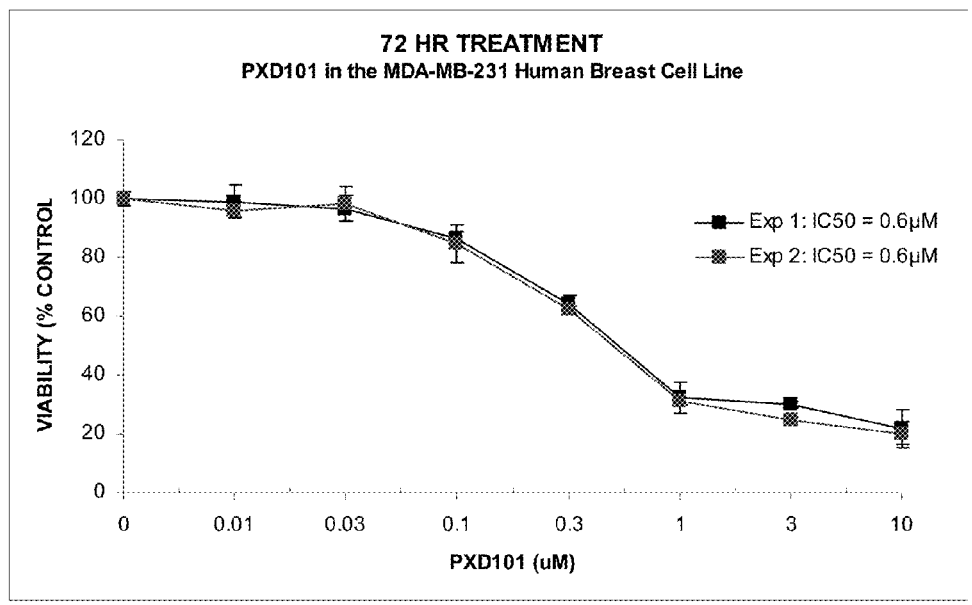
FIG. 7C. Dose response curve of Belinostat in cells from a MDA-MB-231 breast cancer cell lines.
Figure 7D:
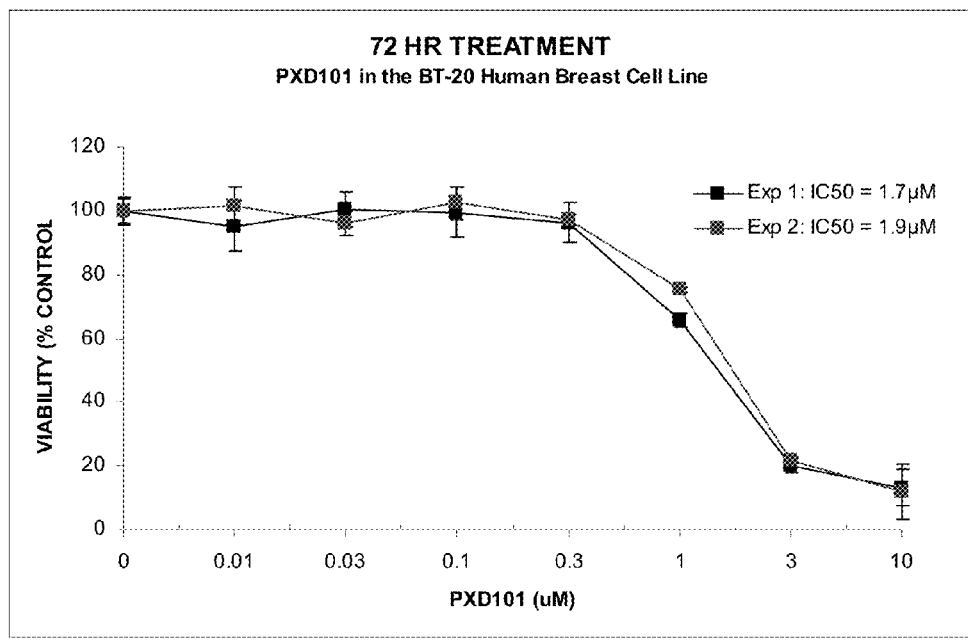
FIG. 7D. Dose response curve of Belinostat in cells from a BT-20 breast cancer cell lines.

The combination of Lucanthone and Belinostat resulted in decreased cell viability (FIG. 7A) and increased apoptosis (FIG. 7B). These data provide evidence that inhibition of autophagy with Lucanthone can successfully augment the anticancer activity of Belinostat.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating a cancer, wherein the cancer is a lung cancer, a brain cancer, a central nervous system cancer, a breast cancer, a colon cancer, a leukemia, a myeloma, a prostate, or an ovarian cancer, the method comprising:
   a) administering an effective amount of a thioxanthone-based autophagy inhibitor selected from 1-((2-(Diethylamino)ethyl)amino)-4-methylthioxanthen-9-one, 1-(2-diethylaminoethylamino)-4-(hydroxymethyl)-9-thioxanthenone, N-[[1-[[2-(diethylamino)ethyl]amino]-9-oxo-9H-thiaxanthen-4-yl]methyl]methanesulfonamide, indazole analogues thereof, or salts thereof, to a mammal in need thereof; and
   b) administering an effective amount of a cancer therapeutic autophagy inducing compound to a mammal in need thereof;
   wherein the administration of both the thioxanthone-based autophagy inhibitor and the cancer therapeutic autophagy inducing compound reduces a symptom associated with the cancer, thereby treating the cancer.

2. The method of claim 1, wherein the thioxanthone-based autophagy inhibitor is 1-((2-(Diethylamino)ethyl)amino)-4-methylthioxanthen-9-one, 1-(2-diethylaminoethylamino)-4-(hydroxymethyl)-9-thioxanthenone, N-[[1-[[2-(diethylamino)ethyl]amino]-9-oxo-9H-thiaxanthen-4-yl]methyl]meth anesulfonamide, indazole analogues thereof, or salts thereof.

3. The method of claim 1, wherein the cancer therapeutic autophagy inducing compound is an arsenic trioxide, an etoposide, a rapamycin, a histone deacetylase inhibitor, a tyrosine kinase inhibitors, a tamoxifen, a temozolomide, an imatinib, or a bortezomib.

4. The method of claim 3, wherein the histone deacetylase inhibitor is a hydroxamate-type histone deacetylase inhibitor or a benzamide-type histone deacetylase inhibitor.

5. The method of claim 3, wherein the histone deacetylase inhibitor is (2E,4E,6R)-7-(4-dimethylaminophenyl)-N-hydroxy-4,6-dimethyl-7-oxohepta-2,4-dienamide, N-hydroxy-N'-phenyloctanediamide, 4-Dimethylamino-N-(6-hydroxycarbamoylhexyl)-benzamide, N-hydroxy -3-[(E)-3-(hydroxyamino)-3-oxoprop-1-enyl]benzamide, (2E)-3-[3-(anilinosulfonyl) phenyl]-N-hydroxyacrylamide, ((E)-N-hydroxy-3-[4-[[2-hydroxyethyl-[2-(1H-indol-3-yl)ethyl] amino]methyl]phenyl]prop-2-enamide, (E)-N-hydroxy-3-[4-[[2-(2-methyl-1H-indol-3-yl)ethylamino]methyl]phenyl]prop-2-enamide, N-(2-aminophenyl)-N'-phenyl-octanediamide, 4-(2-aminophenylcarbamoyl) benzylcarbamate, 4-acetamido-N-(2aminophenyl) benzamide, N-(2-aminophenyl)-4-[[(4-pyridin-3-ylpyrimidin-2-yl)amino]methyl]benzamide, 3-(dimethylaminomethyl)-N-[2-[4-(hydroxycarbamoyl) phenoxy]ethyl]-1-benzofuran-2-carboxamide, or {6-[(diethylamino)methyl]-2-naphthyl}methyl {4-[(hydroxyamino) carbonyl]phenyl}carbamate, or salts thereof.

6. The method of claim 1, wherein the thioxanthone-based autophagy inhibitor and the cancer therapeutic autophagy inducing compound are administered concurrently.

7. The method of claim 1, wherein the thioxanthone-based autophagy inhibitor and the cancer therapeutic autophagy inducing compound are administered sequentially.

8. The method of claim 6, wherein the thioxanthone-based autophagy inhibitor and cancer therapeutic autophagy inducing compound are administered within about three hours of each other.

9. The method of claim 6, wherein the thioxanthone-based autophagy inhibitor and the cancer therapeutic autophagy inducing compound are administered within about two hours of each other.

10. The method of claim 6, wherein the thioxanthone-based autophagy inhibitor and cancer therapeutic autophagy inducing compound are administered within about one hour of each other.

11. The method of claim 1, wherein the cancer is a lung cancer, a brain cancer, a central nervous system cancer, a breast cancer, a colon cancer, a leukemia, a myeloma, a prostate, or an ovarian cancer.

12. The method of claim 11, wherein the lung cancer is non-small lung carcinoma.

13. The method of claim 1, wherein said therapeutically effective amount of the thioxanthone-based autophagy inhibitor and the therapeutically effective amount of the cancer therapeutic autophagy inducing compound are administered in a single daily dose or divided into more than one daily dose.

14. The method of claim 13, wherein said more than one daily dose is two daily doses.

15. The method of claim 1, wherein the thioxanthone-based autophagy inhibitor and the cancer therapeutic autophagy inducing compound are administered orally.

16. The method of claim 1, wherein the thioxanthone-based autophagy inhibitor and the cancer therapeutic autophagy inducing compound are administered parenterally.

17. The method of claim 1, wherein the thioxanthone-based autophagy inhibitor and the cancer therapeutic autophagy inducing compound are administered in the form of a capsule or tablet.

18. The method of claim 1, wherein the thioxanthone-based autophagy inhibitor and the cancer therapeutic autophagy inducing compound are administered for one or more cycles.

19. The method of claim 18, wherein said one cycle comprises 7 times every 4 days.

20. The method of claim 1, further comprising administering radiotherapy.

21. The method of claim 1, wherein the reduction of a symptom associated with cancer using the thioxanthone-based autophagy inhibitor occurs independent of the functional status of p53 activity.

* * * * *